US010602916B2

(12) United States Patent
Ito et al.

(10) Patent No.: US 10,602,916 B2
(45) Date of Patent: Mar. 31, 2020

(54) ENDOSCOPE SYSTEM THAT ADJUSTS LUMINANCE OF FRAME IMAGE INCLUDING IMAGES OF A PLURALIRY OF REGIONS AND ACTUATING METHOD FOR ENDOSCOPE SYSTEM

(71) Applicant: OLYMPUS CORPORATION, Tokyo (JP)

(72) Inventors: Takashi Ito, Hachioji (JP); Kazuki Honda, Higashiyamato (JP)

(73) Assignee: OLYMPUS CORPORATION, Tokyo (JP)

( * ) Notice: Subject to any disclaimer, the term of this patent is extended or adjusted under 35 U.S.C. 154(b) by 406 days.

(21) Appl. No.: 15/448,764

(22) Filed: Mar. 3, 2017

(65) Prior Publication Data
US 2017/0172392 A1    Jun. 22, 2017

Related U.S. Application Data

(63) Continuation of application No. PCT/JP2015/075215, filed on Sep. 4, 2015.

(30) Foreign Application Priority Data

Sep. 8, 2014   (JP) ................................ 2014-182417

(51) Int. Cl.
*A61B 1/04* (2006.01)
*H04N 5/235* (2006.01)
(Continued)

(52) U.S. Cl.
CPC .................. *A61B 1/04* (2013.01); *A61B 1/00* (2013.01); *A61B 1/00006* (2013.01);
(Continued)

(58) Field of Classification Search
CPC ........ G09G 2320/0271; A61B 1/00009; A61B 1/00174; A61B 1/045; A61B 1/06;
(Continued)

(56) References Cited

U.S. PATENT DOCUMENTS 5,940,126 A * 8/1999 Kimura ................ H04N 5/2253
                                                  348/294
6,694,051 B1 * 2/2004 Yamazoe ................ G06T 5/009
                                                  358/1.9
(Continued)

FOREIGN PATENT DOCUMENTS

EP          1548646 A2    6/2005
JP       2001-290103 A   10/2001
(Continued)

OTHER PUBLICATIONS

International Search Report dated Dec. 8, 2015 issued in PCT/JP2015/075215.

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

An endoscope system includes an image forming section configured to arrange first and second images obtained by picking up images of first and second regions of a subject to be adjacent to each other to form an image of one frame, a light source section configured to emit illumination light based on a brightness evaluation of the image to the first and second regions, a brightness-range calculating section configured to detect minimum and maximum luminance values in the first and second images, and an image processing section configured to perform a luminance shift such that a minimum or maximum luminance value of an image, a luminance range of which is smaller than a predetermined luminance range, among the first and second images coincides with a predetermined luminance lower limit or upper limit value.

15 Claims, 16 Drawing Sheets

(51) Int. Cl.

| | | |
|---|---|---|
| *A61B 1/00* | (2006.01) | |
| *A61B 1/06* | (2006.01) | |
| *H04N 5/232* | (2006.01) | |
| *A61B 1/07* | (2006.01) | |
| *A61B 1/05* | (2006.01) | |
| *H04N 5/243* | (2006.01) | |
| *H04N 5/225* | (2006.01) | |
| *A61B 1/045* | (2006.01) | |
| *G02B 23/24* | (2006.01) | |
| *G06T 5/00* | (2006.01) | |

(52) U.S. Cl.
CPC ........ *A61B 1/00009* (2013.01); *A61B 1/0014* (2013.01); *A61B 1/00101* (2013.01); *A61B 1/00181* (2013.01); *A61B 1/045* (2013.01); *A61B 1/05* (2013.01); *A61B 1/053* (2013.01); *A61B 1/06* (2013.01); *A61B 1/0607* (2013.01); *A61B 1/0615* (2013.01); *A61B 1/0669* (2013.01); *A61B 1/07* (2013.01); *G02B 23/2415* (2013.01); *G02B 23/2461* (2013.01); *G02B 23/2484* (2013.01); *G06T 5/009* (2013.01); *H04N 5/2256* (2013.01); *H04N 5/2354* (2013.01); *H04N 5/23232* (2013.01); *H04N 5/243* (2013.01); *G06T 2207/10068* (2013.01); *G06T 2207/20208* (2013.01); *H04N 2005/2255* (2013.01)

(58) Field of Classification Search
CPC .. A61B 1/0661; B41M 2205/22; G06T 5/009; H04N 5/243
See application file for complete search history.

(56) References Cited

U.S. PATENT DOCUMENTS

| | | | | |
|---|---|---|---|---|
| 9,019,433 | B2 * | 4/2015 | Sugimoto | G09G 5/10 348/700 |
| 2003/0020974 | A1 * | 1/2003 | Matsushima | G06T 5/008 358/521 |
| 2005/0128539 | A1 * | 6/2005 | Takano | H04N 1/6027 358/521 |
| 2005/0141002 | A1 * | 6/2005 | Takano | G06T 5/008 358/1.9 |
| 2005/0141780 | A1 * | 6/2005 | Takahashi | G06T 5/009 382/260 |
| 2006/0023273 | A1 * | 2/2006 | Kato | H04N 1/4074 358/519 |
| 2006/0215908 | A1 * | 9/2006 | Kamon | H04N 1/6088 382/167 |
| 2007/0040914 | A1 * | 2/2007 | Katagiri | H04N 5/243 348/221.1 |
| 2009/0073287 | A1 * | 3/2009 | Shimizu | H04N 5/23212 348/234 |
| 2009/0073469 | A1 * | 3/2009 | Kita | G03G 15/5029 358/1.9 |
| 2011/0267542 | A1 * | 11/2011 | Tada | H04N 5/202 348/672 |
| 2011/0273549 | A1 * | 11/2011 | Kase | A61B 1/00147 348/68 |
| 2012/0253121 | A1 * | 10/2012 | Kitano | A61B 1/00188 600/109 |
| 2014/0330078 | A1 * | 11/2014 | Hwang | A61B 1/00193 600/111 |
| 2015/0356904 | A1 * | 12/2015 | Nakatani | G09G 5/377 345/690 |
| 2016/0015258 | A1 * | 1/2016 | Levin | A61B 1/00006 600/109 |
| 2016/0054969 | A1 * | 2/2016 | Maruyama | G06F 3/1423 345/690 |

FOREIGN PATENT DOCUMENTS

| | | |
|---|---|---|
| JP | 2002-017667 A | 1/2002 |
| JP | 2005-192154 A | 7/2005 |
| JP | 2006-033520 A | 2/2006 |
| JP | 2007-190060 A | 8/2007 |
| JP | 4782900 B2 | 9/2011 |
| JP | 2012-157577 A | 8/2012 |
| JP | 2013-066648 A | 4/2013 |
| JP | 2013-542467 A | 11/2013 |
| WO | WO 2011/055613 A1 | 5/2011 |

* cited by examiner

ENDOSCOPE SYSTEM THAT ADJUSTS LUMINANCE OF FRAME IMAGE INCLUDING IMAGES OF A PLURALIRY OF REGIONS AND ACTUATING METHOD FOR ENDOSCOPE SYSTEM

CROSS REFERENCE TO RELATED APPLICATION

This application is a continuation application of PCT/JP2015/075215 filed on Sep. 4, 2015 and claims benefit of Japanese Application No. 2014-182417 filed in Japan on Sep. 8, 2014, the entire contents of which are incorporated herein by this reference.

BACKGROUND OF THE INVENTION

1. Field of the Invention

The present invention relates to an endoscope system that acquires a first image and a second image in different regions in a same subject and an actuating method for the endoscope system.

2. Description of the Related Art

In recent years, in order to enable observation of a wider range, a wide angle endoscope including a front-view observation optical system and a side-view observation optical system has been proposed.

Examples of the wide angle endoscope include, for example, a type for forming, on one image pickup device, a front-view subject image via a front-view observation window and a side-view subject image via a side-view observation window described in Japanese Patent No. 4782900, and a type in which cameras obtained by combining optical systems and image pickup devices are provided respectively for front view and side view described in Japanese Patent Application Laid-Open Publication No. 2013-542467 (International Publication No. 2012/056453).

Incidentally, when a subject is irradiated by light having constant luminance, in general, illuminance is high in a proximity portion and is low in a remote portion. The proximity portion is more brightly observed and the remote portion is more darkly observed. More specifically, when, for example, a subject having a luminal shape is observed using the wide angle endoscope, an observation region by front view is a remote portion in the axial direction of a lumen and is dark and an observation region by side view is a proximity portion of a lumen inner wall and is bright.

Therefore, for example, International Publication No. 2011/055613 describes an endoscope system that individually detects brightness of a front-view field of view image and brightness of a side-view field of view image and controls, on the basis of a detection result, a light source device such that one field of view image reaches a brightness target value suitable for observation.

Japanese Patent Application Laid-Open Publication No. 2013-066648 describes an image processing apparatus for endoscopes that acquires a forward image corresponding to a forward field of view and a sideward image corresponding to a sideward field of view, performs forward magnification chromatic aberration correction processing when a processing target image signal is the forward image, and performs sideward magnification chromatic aberration correction processing when the processing target image signal is the sideward image.

Further, Japanese Patent Application Laid-Open Publication No. 2001-290103 describes a technique for, in an observation system that observes a front-view forward field of view image with light transmitted through a half mirror and observes an endoscopic image of a liquid crystal monitor with light reflected by the half mirror, changing brightness of an image displayed on the liquid crystal monitor to switch the observation of the forward field of view image and the observation of the endoscopic image.

SUMMARY OF THE INVENTION

An endoscope system according to an aspect of the present invention includes: an image forming section configured to form an image of one frame in which a first image obtained by picking up an image of a first region of a subject and a second image obtained by picking up an image of a second region of the subject are arranged to be adjacent to each other; a light source section configured to emit illumination light having brightness based on a brightness evaluation result of the image of the one frame to the first and second regions; a luminance detecting section configured to detect a minimum luminance value and a maximum luminance value in the first image included in the image of the one frame and detect a minimum luminance value and a maximum luminance value in the second image included in the image of the one frame; and an image processing section configured to determine, among the first image and the second image, whether or not a luminance range, which is a difference value between the maximum luminance value and the minimum luminance value, is larger than a predetermined luminance range defined by a difference value between a predetermined luminance upper limit value and a predetermined luminance lower limit value, and perform luminance shift processing such that the minimum luminance value of an image, the luminance range of which is determined as being smaller than the predetermined luminance range, among the first image and the second image coincides with the predetermined luminance lower limit value or such that the maximum luminance value of the image coincides with the predetermined luminance upper limit value.

An actuating method for an endoscope system according to another aspect of the present invention is an actuating method for an endoscope system including an illuminating section configured to radiate light on a first region of a subject and a second region of the subject different from the first region, the actuating method including: a first subject-image acquiring section provided in an insertion section picking up an image of the first region; a second subject-image acquiring section provided in the insertion section picking up an image of the second region; an image forming section arranging a first image picked up by the first subject-image acquiring section and a second image picked up by the second subject-image acquiring section to be adjacent to each other to form an image of one frame; a light source section emitting illumination light having brightness based on a brightness evaluation result of the image of the one frame to the first and second regions; a luminance detecting section detecting a minimum luminance value and a maximum luminance value in the first image included in the image of the one frame and detecting a minimum luminance value and a maximum luminance value in the second image included in the image of the one frame; and an image processing section determining, among the first image and the second image, whether or not a luminance range, which is a difference value between the maximum luminance value and the minimum luminance value, is larger than a predetermined luminance range defined by a difference value between a predetermined luminance upper limit value and a predetermined luminance lower limit value, and performing luminance shift processing such that the minimum luminance value of an image, the luminance range of which is determined as being smaller than the predetermined luminance range, among the first image and the second image coincides with the predetermined luminance lower limit value or such that the maximum luminance value of the image coincides with the predetermined luminance upper limit value.

DETAILED DESCRIPTION OF THE PREFERRED EMBODIMENT(S)

An embodiment of the present invention is explained below with reference to the drawings.

[First Embodiment]

Figure 1:
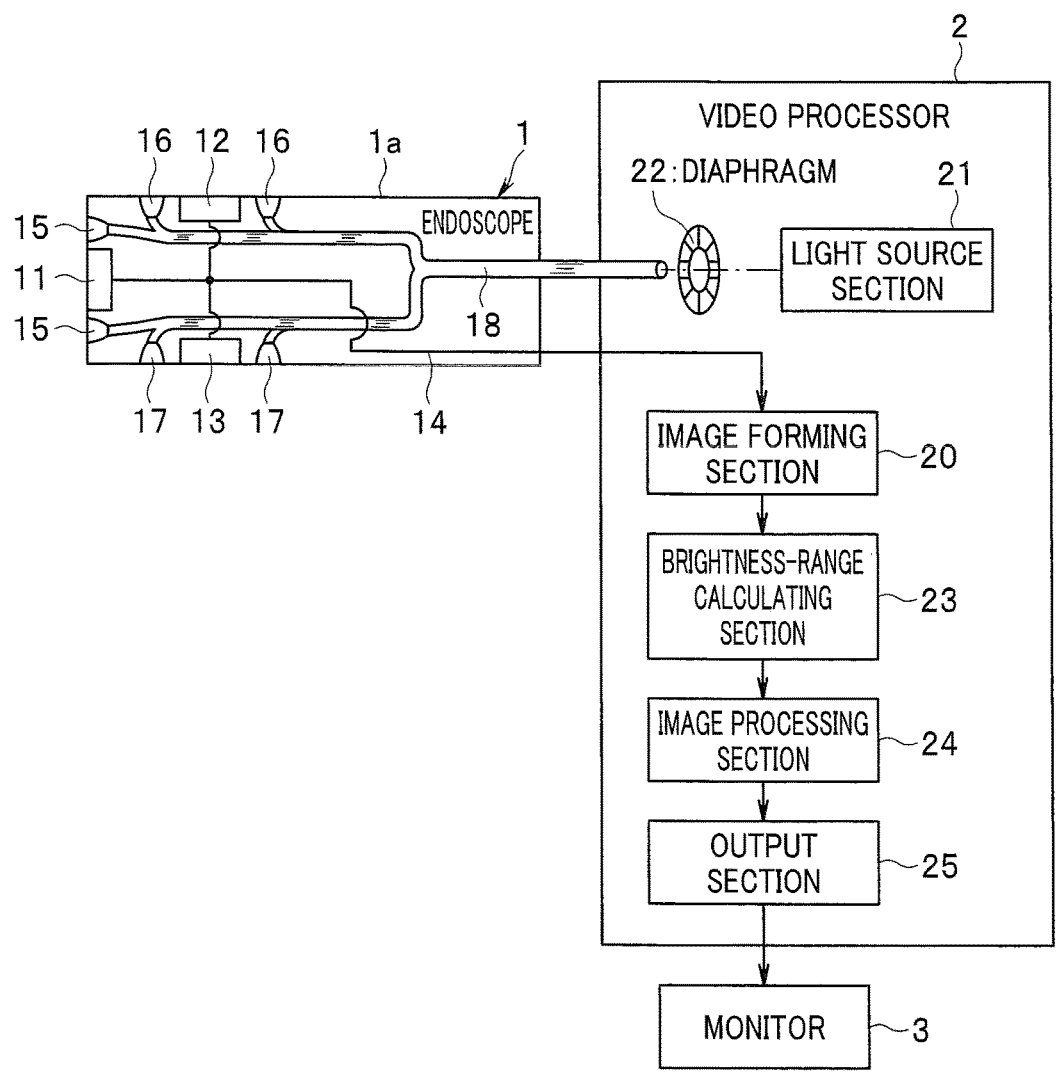
FIG. 1 is a diagram showing a configuration of an endoscope system in a first embodiment of the present invention.

FIGS. 1 to 18 show a first embodiment of the present invention. FIG. 1 is a diagram showing a configuration of an endoscope system.

The endoscope system includes an endoscope 1, a video processor 2, and a monitor 3.

The endoscope 1 is configured as an electronic endoscope including an insertion section 1a inserted into an inside of a subject. The endoscope 1 includes a first subject-image acquiring section provided in the insertion section 1a, the first subject-image being configured to acquire section acquiring a first picked-up image related to a first subject image (optical image) of a first region in the subject, a second subject-image acquiring section provided in the insertion section 1a, the second subject-image acquiring section being configured to acquire a second image pickup signal related to a second subject image (optical image) of a second region in the subject different from the first region, and an illuminating section configured to radiate light on the first region and the second region.

More specifically, an example of the first region is a region including a forward direction (a region of a forward field of view) in the subject. The first subject-image acquiring section includes an image pickup section 11 (a first image pickup section) disposed to be directed forward at a distal end portion of the insertion section 1a, the image pickup section 11 being configured to photoelectrically convert the first subject image (optical image) of the first region in the subject including a forward direction along a longitudinal direction of the insertion section 1a and generating the first image pickup signal.

An example of the second region different from the first region is a region including a sideward direction (a region of a sideward field of view) in the same subject. The second subject-image acquiring section photoelectrically converts the second subject image (optical image) in the second region in the subject including the sideward direction crossing the longitudinal direction of the insertion section 1a to generate the second image pickup signal. More specifically, the second subject-image acquiring section is disposed in plurality in a plurality of angle positions in a circumferential direction of the insertion section 1a and acquires a plurality of second image pickup signals related to a plurality of second subject images. In particular, the second subject-image acquiring section include an image pickup section 12 (a second image pickup section separate from the first image pickup section) that picks up an image of a field of view region in a right sideward direction and an image pickup section 13 (a second image pickup section separate from the first image pickup section) that picks up an image of a field of view region in a left sideward direction.

The right sideward field of view and the left sideward field of view are, for example, equally divided two positions in the circumferential direction centering on a forward field of view.

The image pickup sections 11 to 13 include image pickup optical systems and image pickup devices. The image pickup sections 11 to 13 photoelectrically convert, with the image pickup devices, subject images formed by the image pickup optical systems to generate image pickup signals and output the generated image pickup signals to the video processor 2 via a signal line 14.

Note that in an example explained above, the first subject-image acquiring section and the second subject-image acquiring section respectively include the image pickup optical systems and the image pickup devices. However, first subject-image acquiring section and the second subject-image acquiring section may share at least one of the image pickup optical system and the image pickup device. That is, although the first subject-image acquiring section and the second subject-image acquiring section acquire optical images in respective directions of fields of view, the first subject-image acquiring section and the second subject-image acquiring section may share at least a part of the image pickup optical system or may form optical images respectively acquired by the first subject-image acquiring section and the second subject-image acquiring section in different regions on the same image pickup device shared by the first subject-image acquiring section and the second subject-image acquiring section.

As the illuminating section, an illuminating section 15 that radiates light on an image pickup range by the image pickup section 11, an illuminating section 16 that radiates light on an image pickup range by the image pickup section 12, and an illuminating section 17 that radiates light on an image pickup range by the image pickup section 13 are provided. Therefore, the illuminating section 15 illuminates a forward direction, the illuminating section 16 illuminates a right sideward direction, and the illuminating section 17 illuminates a left sideward direction. In the example shown in FIG. 1, the illuminating sections 15, 16, and 17 are provided in plurality around the image pickup sections 11, 12, and 13 in order to reduce illumination unevenness.

Illumination light from the video processor 2 is supplied to the illuminating sections 15, 16, and 17 via a light guide 18 configured as an optical fiber bundle. For example, a proximal end side of the light guide 18 is converged and a distal end side of the light guide 18 branches to the respective illuminating sections 15, 16, and 17.

On the other hand, the video processor 2 includes an image forming section 20, a light source section 21, a diaphragm 22, a brightness-range calculating section 23, an image processing section 24, and an output section 25.

The light source section 21 generates illumination light and emits the illumination light as parallel rays via a collimator lens or the like.

The diaphragm 22 limits a passing range of the illumination light emitted from the light source section 21 to thereby control a light amount of the illumination light that reaches the proximal end of the light guide 18. As explained above, the distal end side of the light guide 18 branches to be connected to the respective illuminating sections 15, 16, and 17. Therefore, in the configuration example shown in FIG. 1, adjustment of light amounts of the illumination lights radiated from the respective illuminating sections 15, 16, and 17 on the subject is performed by simultaneously increasing the light amounts or performed by simultaneously reducing the light amounts.

The image forming section 20 forms a first image and a second image on the basis of image pickup signals corresponding to different regions in a same subject. The image forming section 20 receives a first image pickup signal from a first image pickup section electrically connected via the signal line 14 to form a first image (image signal) and receives a second image pickup signal from second image pickup sections to form second images (image signals). The image forming section 20 forms, on the basis of the first image and the second images, an image in which the first image is set in the center and a plurality of second images are respectively arranged in a plurality of angle positions in the circumferential direction of the first image according to respective directions of fields of view of the image pickup sections 11 to 13.

More specifically, the image forming section 20 includes, for example, a frame buffer. The image forming section 20 stores, in addresses corresponding to pixel positions in the frame buffer, image pickup signals sequentially inputted, for example, in pixel units from the image pickup sections 11 to 13 to thereby form an image for one frame formed by respective pixels of the first image and respective pixels of the second images.

The brightness-range calculating section 23 is a luminance detecting section that detects minimum luminance values and maximum luminance values in the first image and the second images. More specifically, the brightness-range calculating section 23 calculates a brightness range by detecting a minimum luminance value and a maximum luminance value of a pixel (excluding an excluded region explained below) out of all the pixels forming the images (the first image and the second images) formed by the image forming section 20 on the basis of the image pickup signals obtained from the respective image pickup sections 11, 12, and 13.

The image processing section 24 receives an image signal (an image) from the image forming section 20 electrically connected via the brightness-range calculating section 23. The image processing section 24 sets a predetermined luminance range and subjects the first image and the second images to gradation conversion such that a luminance range from the minimum luminance value to the maximum luminance value is fit within a predetermined luminance range. An example of the predetermined luminance range is a proper luminance range from a proper lower limit luminance value to a proper upper limit luminance value.

The proper luminance range is a luminance range set assuming that a three-dimensional appearance (feeling of convex-concave) and a distance feeling can be reproduced and a displayed image is suitable for observation. The proper upper limit luminance value is an upper limit value of luminance set assuming that the upper limit value is suitable for observation of the subject. The proper lower limit luminance value is a lower limit value of luminance set assuming that the lower limit value is suitable for the observation of the subject.

The image processing section 24 performs not only the gradation conversion but also general various kinds of image processing and the like.

Note that details of the processing by the brightness-range calculating section 23 and the image processing section 24 are more specifically explained below according to flowcharts of FIGS. 10 to 12.

The output section 25 is an image output section that generates, on the basis of the image subjected to the gradation conversion by the image processing section 24, a display signal for causing the monitor 3 to display the image.

Receiving the display signal outputted from the output section 25, the monitor 3 functioning as a display section displays the image fit within the proper luminance range while maintaining a luminance magnitude relation among the pixels. Therefore, an observer can observe, at proper brightness, an image having shading and three-dimensional appearance with which a diagnosis is easily performed.

Figure 2:
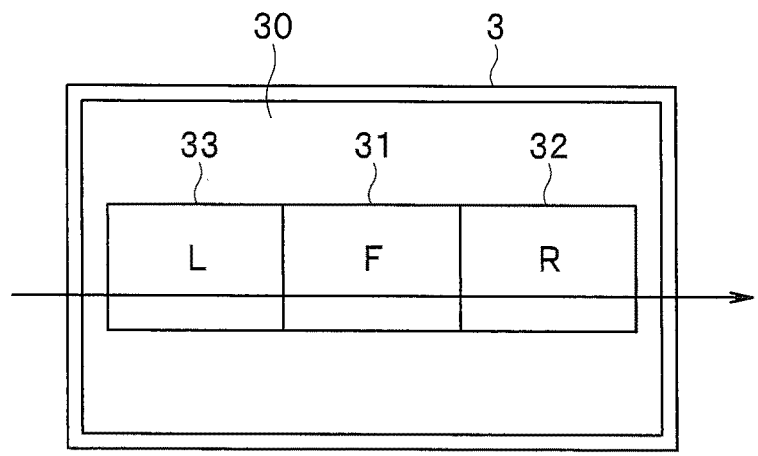
FIG. 2 is a diagram showing a display example of a screen of a monitor in the first embodiment.

FIG. 2 is a diagram showing a display example of a screen 30 of the monitor 3. Note that, in FIGS. 2 and 3 referred to below, a forward direction is indicated by F, a right sideward direction is indicated by R, and a left sideward direction is indicated by L.

On the screen 30 of the monitor 3, a forward image 31 (based on the first image) based on the image pickup signal obtained from the image pickup section 11 is arranged and displayed in the center, a right sideward image 32 based on the image pickup signal obtained from the image pickup section 12 is arranged and displayed on the right of the forward image 31, and a left sideward image 33 based on the image pickup signal obtained from the image pickup section 13 is arranged and displayed on the left of the forward image 31 (the right sideward image 32 and the left sideward image 33 are respectively based on the second images). That is, the image forming section 20 forms an image such that the first image and the second images are arranged to be adjacent to each other in the same screen. Arrangement of the respective images 31 to 33 viewed from the observer is arrangement coinciding with respective directions of fields of view viewed from the endoscope 1. An image configuration is realized as if an observation is performed by one super-wide angle camera. Note that, in the example shown in FIG. 2, the forward image 31, the right sideward image 32, and the left sideward image 33 are displayed on the screen 30 of one monitor 3. However, the forward image 31, the right sideward image 32, and the left sideward image 33 may be respectively displayed on screens of separate monitors.

Figure 3:
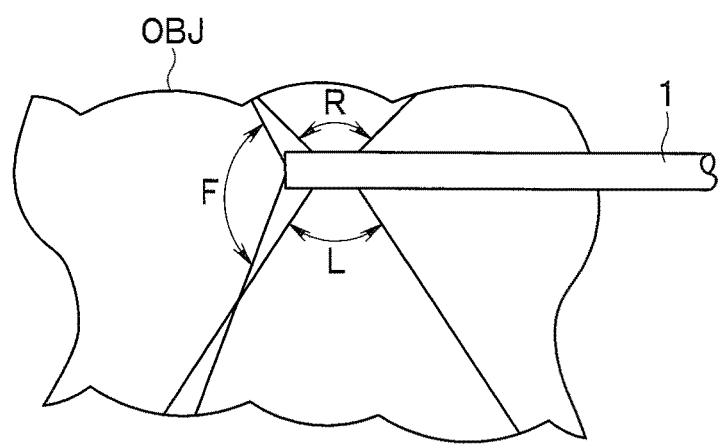
FIG. 3 is a top view of a situation in which an endoscope is inserted in a state in which the endoscope is in close proximity to an inner wall on a right side of a subject formed in a luminal shape in the first embodiment.

FIG. 3 is a top view showing a situation in which the endoscope 1 is inserted in a state in which the endoscope 1 is in close proximity to an inner wall on a right side of a subject OBJ formed in a luminal shape.

At this point, a portion of the subject OBJ present on the right sideward direction R side is a proximity portion and a portion of the subject OBJ present on the left sideward direction L side is a remote portion. The subject OBJ present on the forward direction F side is a remote portion in a center portion and is slightly a proximity portion in a peripheral portion reflecting the fact that the subject OBJ has the luminal shape. In such a state, a dynamic range of a luminance distribution of the subject OBJ easily increases.

Figure 4:
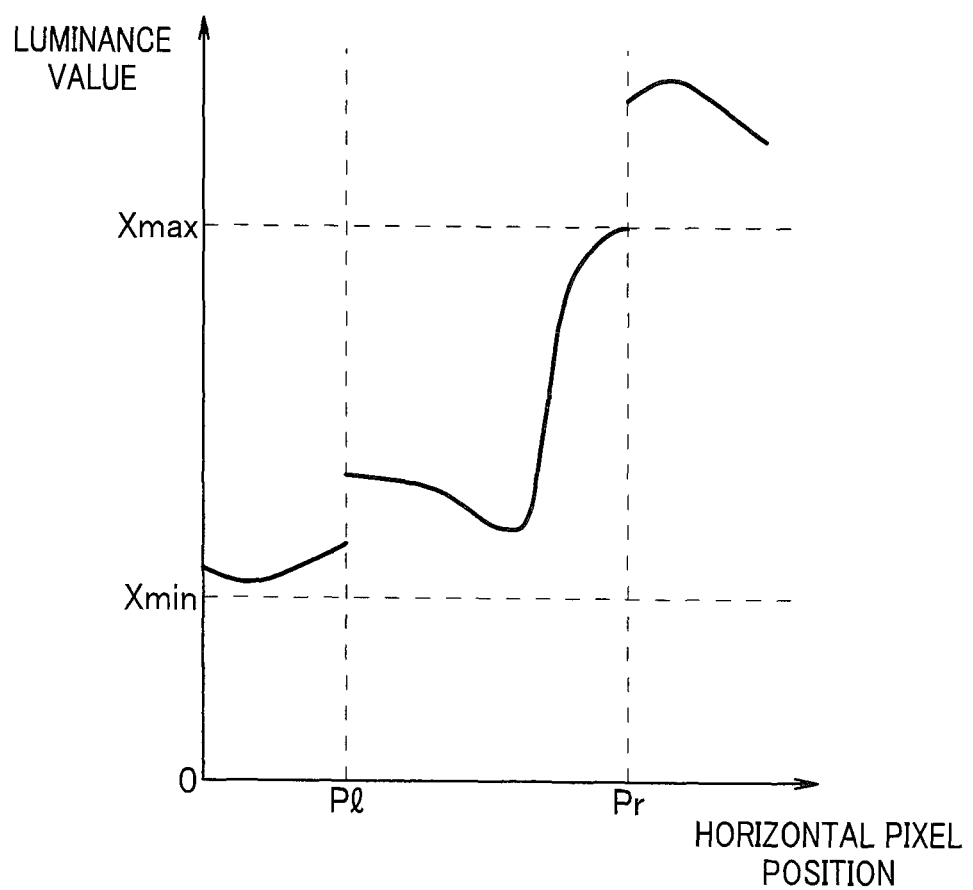
FIG. 4 is a diagram showing an example of a luminance distribution of images obtained in the state shown in FIG. 3 in the first embodiment.

FIG. 4 is a diagram showing an example of a luminance distribution of the images obtained in a state shown in FIG. 3. Note that, in FIGS. 4 and 5 to 7 and 9 referred to below, Pr indicates a horizontal pixel position of a boundary between the forward image 31 and the right sideward image 32 and P1 indicates a horizontal pixel position of a boundary between the forward image 31 and the left sideward image 33. Further, in FIGS. 4 to 9 and 10, Xmax indicates a proper upper limit luminance value, which is an upper limit of a proper luminance range, and Xmin indicates a proper lower limit luminance value, which is a lower limit of the proper luminance range.

In order to clearly display situations of luminance distributions of the respective images 31, 32, and 33 as a diagram, in FIG. 4, the luminance distributions are shown as a continuous luminance distribution. However, pixels as many as rows of the image pickup device are present in a predetermined horizontal position of an image. Therefore, actually, luminance values as many as the rows are distributed in one row of the image. In FIG. 4, for example, an example of a luminance distribution in one row along an arrow shown in FIG. 2 is shown. However, since the respective images 31, 32, and 33 are configured by pluralities of rows, if an x axis indicates a horizontal pixel position and a y axis indicates a luminance value and, further, a z axis is used as an axis indicating a row number, the luminance distribution is a two-dimensional distribution in the three-dimensional coordinate.

In the state shown in FIG. 3, distances from the respective illuminating sections 15, 16, and 17 to the subject OBJ are as explained above. Therefore, a luminance value of the right sideward image 32 on a right side with respect to the horizontal pixel position Pr exceeds the proper upper limit luminance value Xmax. The right sideward image 32 is in a state close to white exceeding a range in which an observation is easily performed. The forward image 31 between the horizontal pixel position P1 and the horizontal pixel position Pr is fit within the proper luminance range. However, a minimum point of a luminance value occurs in a center portion reflecting the fact that the subject OBJ is formed in the luminal shape. Further, a luminance value of the left sideward image 33 on a left side with respect to the horizontal pixel position PI is fit within the proper luminance range but is close to the proper lower limit luminance value Xmin. The left sideward image 33 is a relatively dark image portion. A dynamic range of a luminance distribution of the subject is wider than a dynamic range of the proper luminance range.

Figure 5:
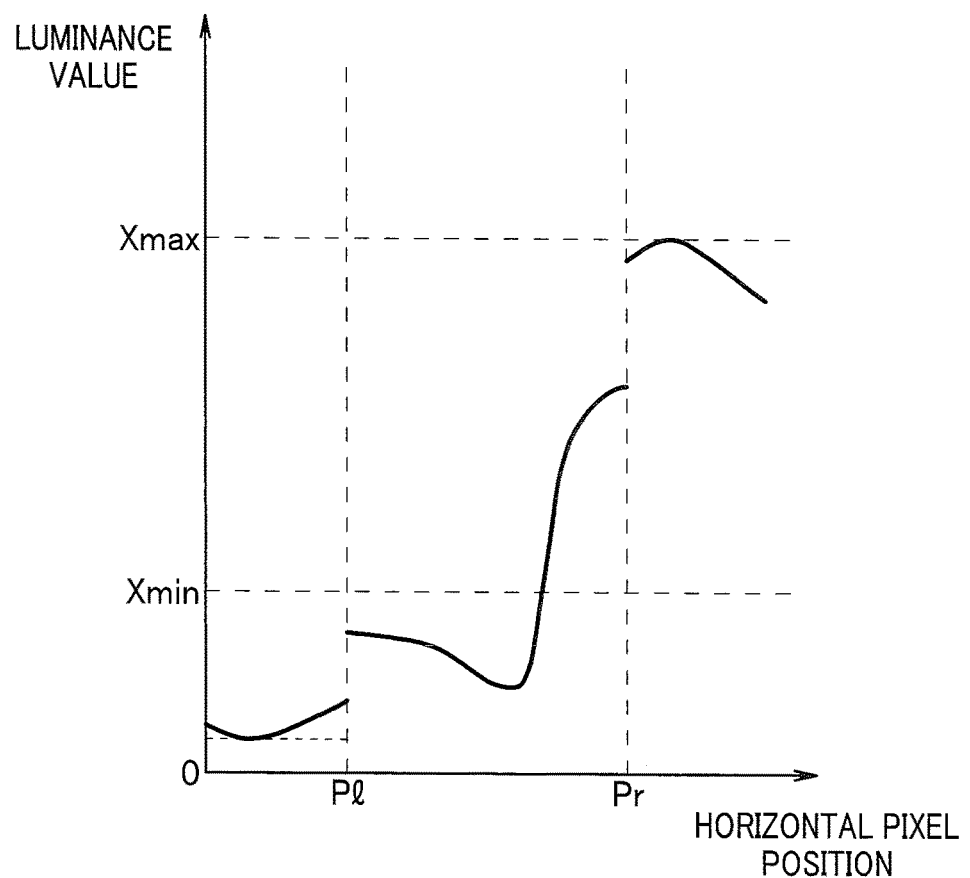
FIG. 5 is a diagram showing an example of a luminance distribution of images obtained in the state shown in FIG. 3 when light adjustment is performed in a peak mode in the first embodiment.
Figure 6:
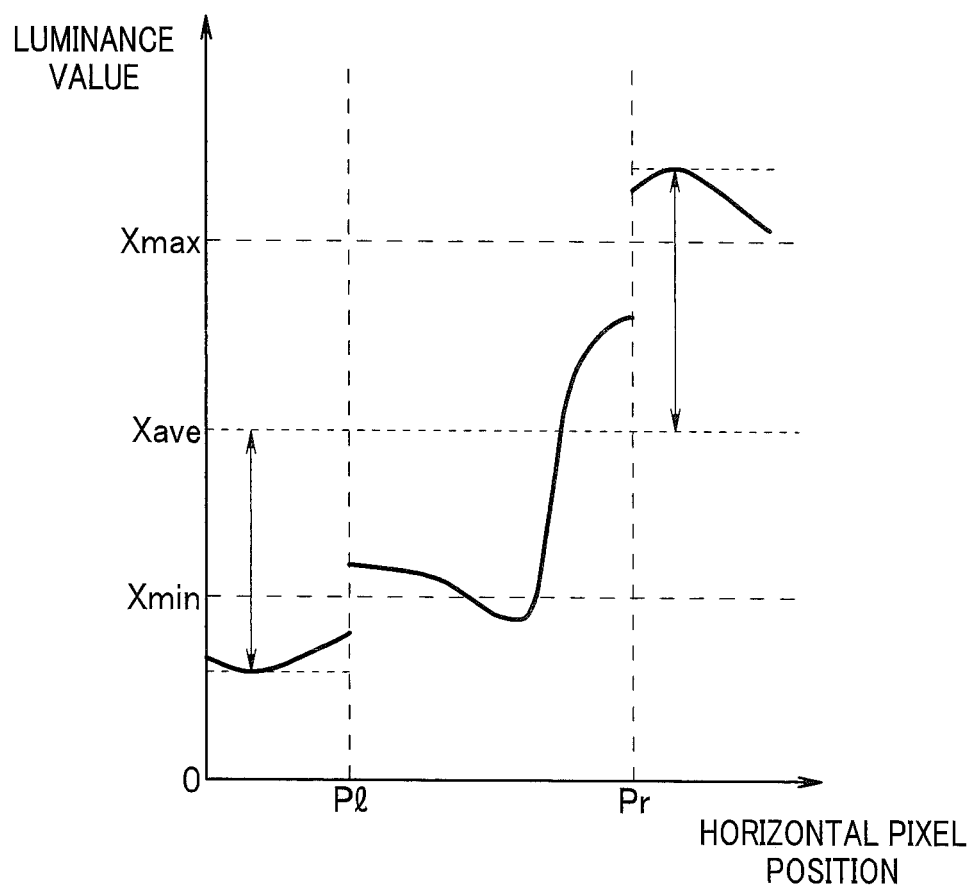
FIG. 6 is a diagram showing an example of a luminance distribution of images obtained in the state shown in FIG. 3 when light adjustment is performed in an average mode in the first embodiment.

FIG. 5 is a diagram showing an example of a luminance distribution of images obtained in the state shown in FIG. 3 when light adjustment is performed in a peak mode. FIG. 6 is a diagram showing an example of a luminance distribution of images obtained in the state shown in FIG. 3 when light adjustment is performed in an average mode.

As a method of adjusting brightness of the images, in general, a peak mode and an average mode are known. The brightness adjustment can be performed by either adjusting illumination light amounts using the diaphragm 22 or shifting a luminance value of the entire images to a bright direction or a dark direction through image processing. It is assumed here that, for example, the brightness adjustment is performed using the diaphragm 22.

First, the peak mode is a method of adjusting brightness of the images such that a maximum luminance value of the images (the forward image 31, the right sideward image 32, and the left sideward image 33) coincides with the proper upper limit luminance value, which is the upper limit of the proper luminance range. A luminance distribution of the images obtained by applying the peak mode to the subject having the luminance distribution shown in FIG. 4 is, for example, as shown in FIG. 5. When the peak mode is applied, an upper limit of the luminance distribution is fit within the proper luminance range. However, a lower limit of the luminance distribution is sometimes smaller than the proper lower limit luminance value Xmin exceeding the proper luminance range as shown in FIG. 5.

On the other hand, the average mode is a method of adjusting brightness of the images such that an average luminance value of the images (the forward image 31, the right sideward image 32, and the left sideward image 33) coincides with a proper average luminance value Xave=

(Xmax+Xmin)/2, which is a center of the proper luminance range. A luminance distribution of the images obtained by applying the average mode to the subject having the luminance distribution shown in FIG. 4 is, for example, as shown in FIG. 6. When the average mode is applied to a subject, a dynamic range of a luminance distribution of which is wider than the dynamic range of the proper luminance range, as shown in FIG. 6, an upper limit of the luminance distribution is sometimes larger than the proper upper limit luminance value Xmax exceeding the proper luminance range and, further, a lower limit of the luminance distribution is sometimes smaller than the proper lower limit luminance value Xmin exceeding the proper luminance range.

Figure 7:
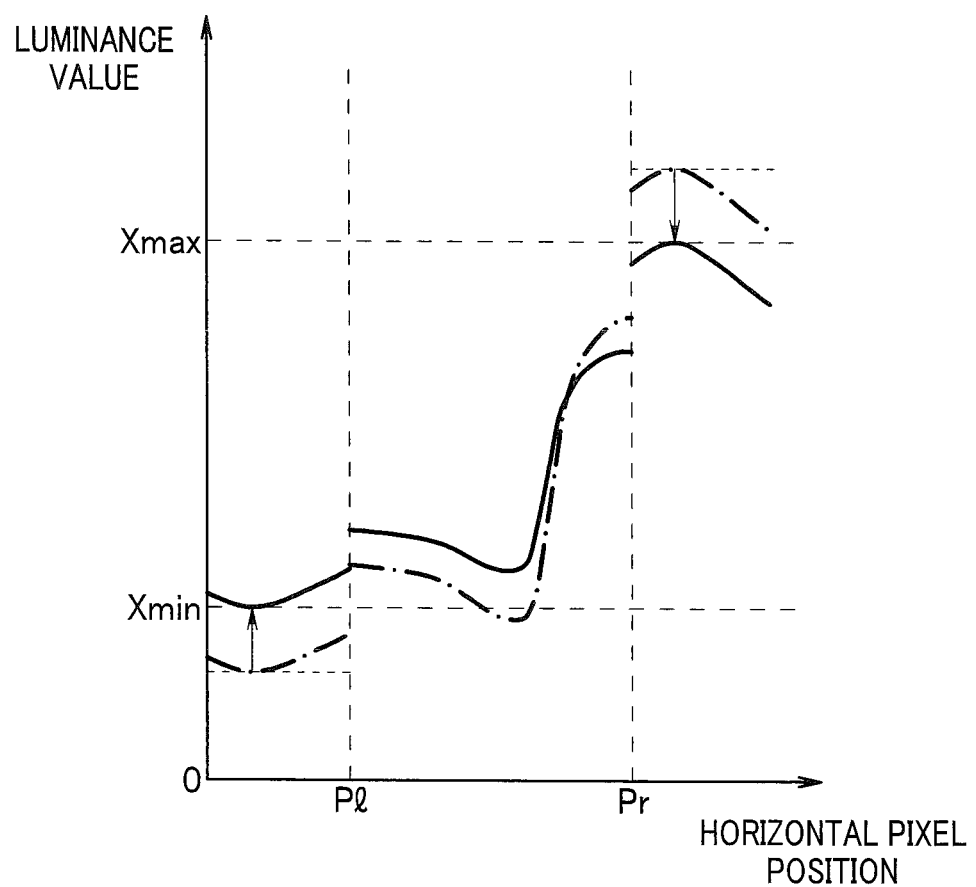
FIG. 7 is a diagram showing a situation of a change of a luminance distribution by gradation conversion in the first embodiment.
Figure 8:
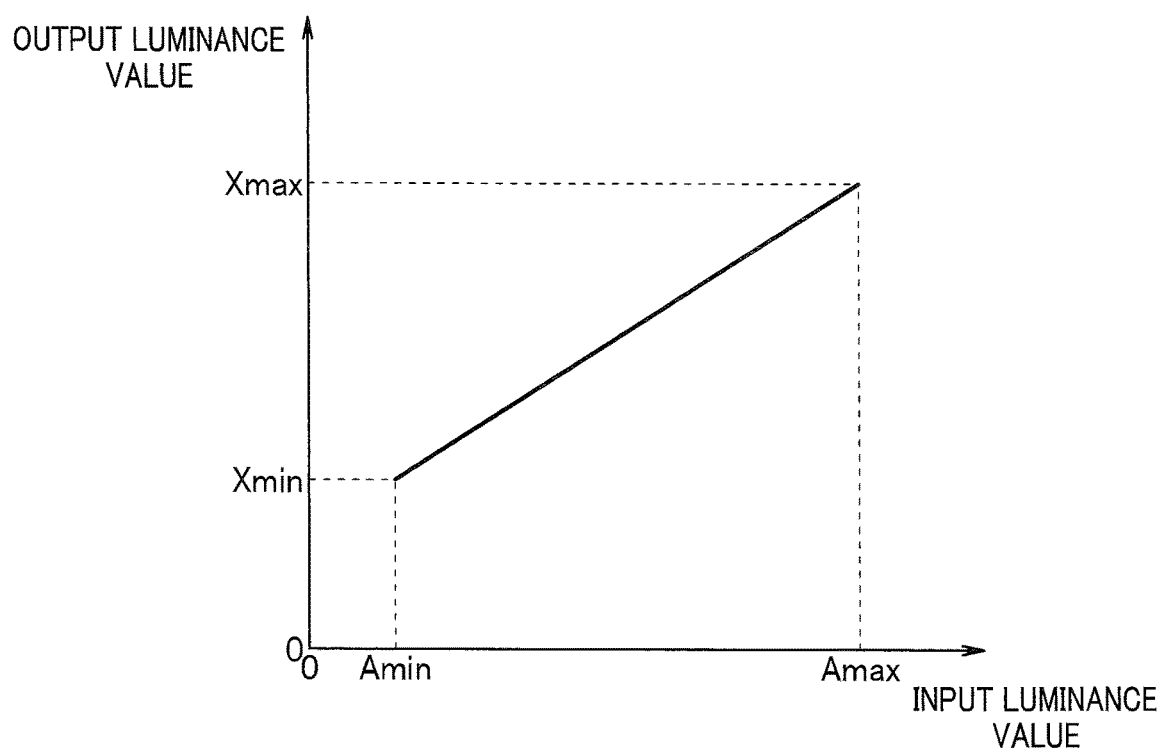
FIG. 8 is a diagram showing an example of a gradation conversion curve for fitting images within a proper luminance range in the first embodiment.
Figure 9:
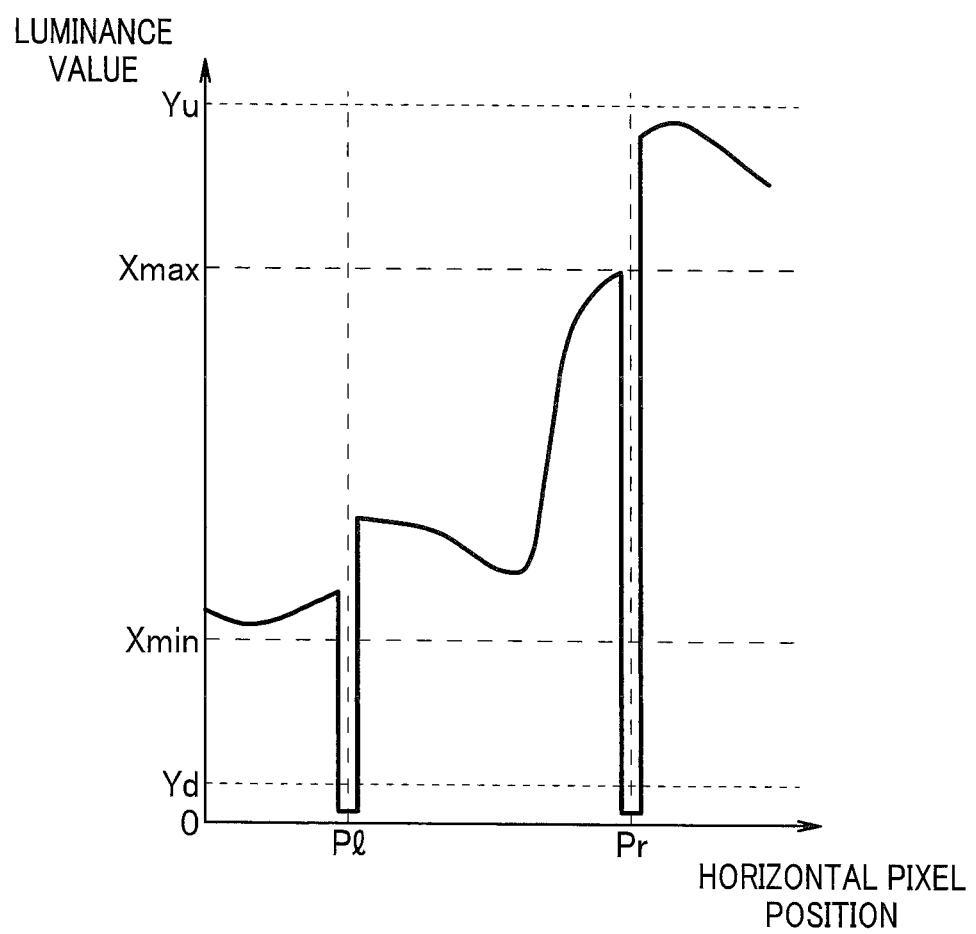
FIG. 9 is a diagram showing an example of a luminance distribution obtained when gaps of black display are present between a forward image and a right sideward image and between the forward image and a left sideward image in the first embodiment.
Figure 10:
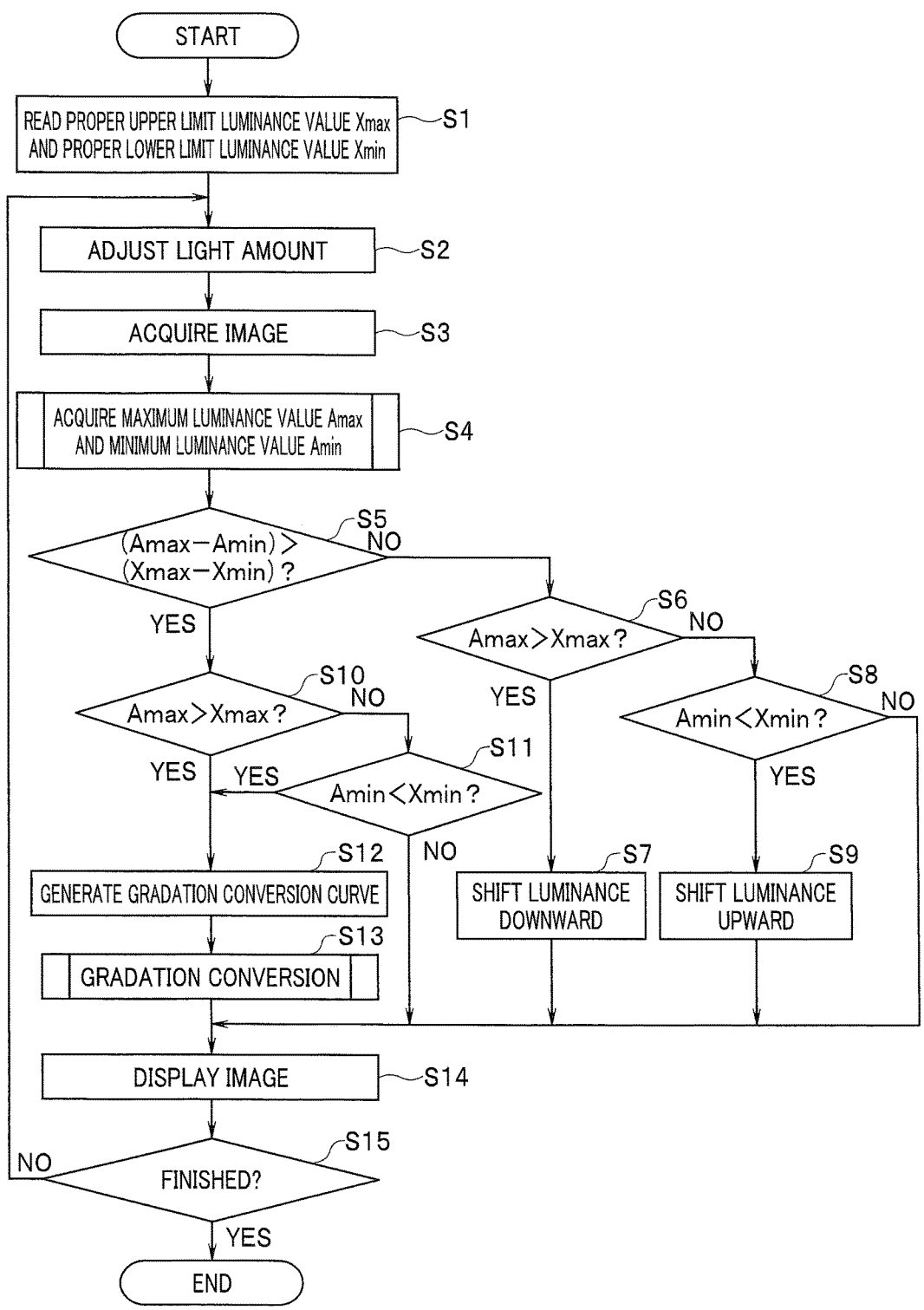
FIG. 10 is a flowchart for explaining processing of luminance adjustment of the endoscope system in the first embodiment.
Figure 11:
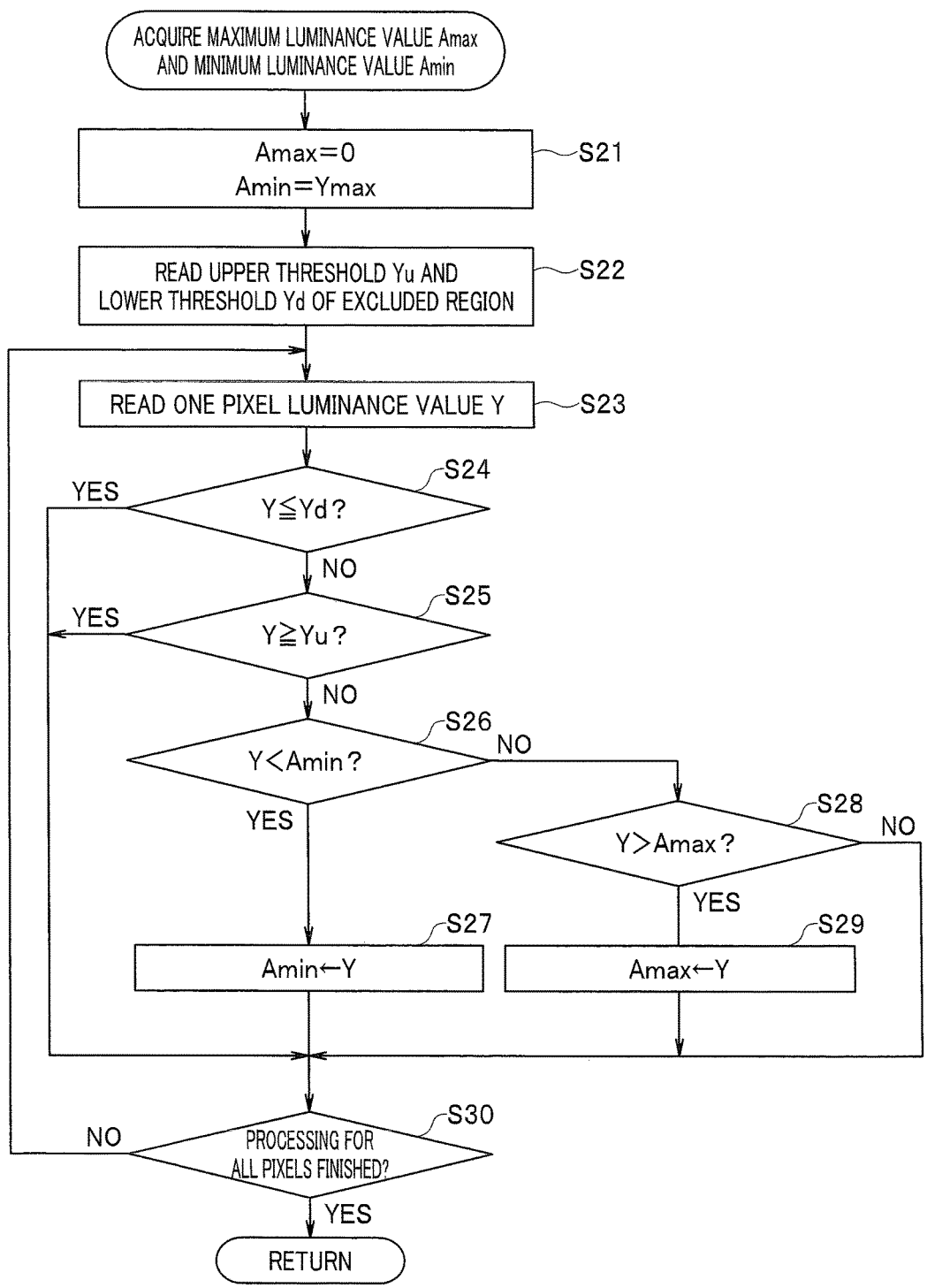
FIG. 11 is a flowchart for explaining details of acquisition processing for a maximum luminance value Amax and a minimum luminance value Amin in step S4 in FIG. 10 in the first embodiment.
Figure 12:
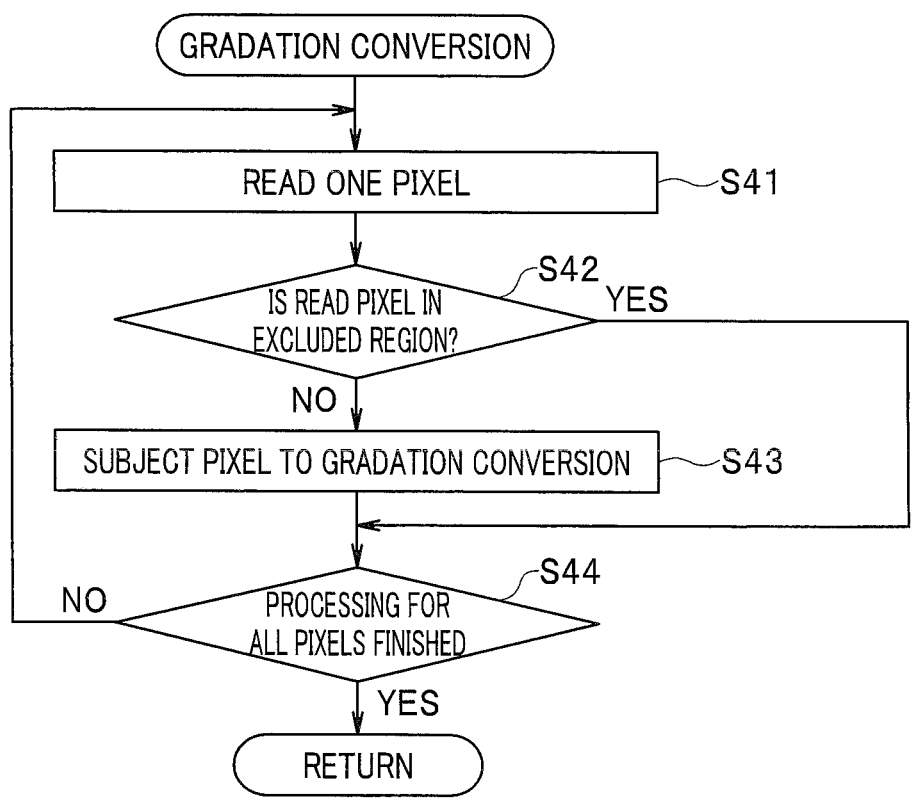
FIG. 12 is a flowchart for explaining details of gradation conversion processing in step S13 in FIG. 10 in the first embodiment.

Action of the endoscope system in the present embodiment is explained according to flowcharts of FIGS. 10 to 12 with reference to FIGS. 7 to 9.

The endoscope system in the present embodiment does not perform processing shown in the flowcharts of FIGS. 10 to 12 as processing for separately fitting an endoscopic image acquired in advance in the proper luminance range later but performs the processing as processing for performing, with the video processor 2, on a real time basis, luminance adjustment of an endoscopic image acquired by the endoscope 1.

First, FIG. 10 is a flowchart for explaining the processing of the luminance adjustment by the endoscope system.

When the processing is started, the brightness-range calculating section 23 reads the proper upper limit luminance value Xmax and the proper lower limit luminance value Xmin set in advance (or set by a user) (step S1).

The endoscope system controls the diaphragm 22 to thereby adjust a light amount of illumination light, for example, in the peak mode or the average mode explained above (step S2).

Thereafter, the endoscope system radiates the illumination light, the light amount of which is adjusted in step S2, from the illuminating sections 15 to 17 on the subject. For example, the endoscope system acquires images of the subject for one frame with the image pickup sections 11 to 13 and the image forming section 20 (step S3).

As explained below with reference to FIG. 11, the brightness-range calculating section 23 compares luminance values of respective pixels in the acquired images (the forward image 31, the right sideward image 32, and the left sideward image 33) to thereby acquire the maximum luminance value Amax and the minimum luminance value Amin (step S4).

Subsequently, the image processing section 24 determines whether a dynamic range (Amax−Amin) of the images is larger than a dynamic range (Xmax−Xmin) of the proper luminance range (step S5).

When determining that (Amax−Amin)≤(Xmax−Xmin), the image processing section 24 determines whether the maximum luminance value Amax of the images is larger than the proper upper limit luminance value Xmax (step S6).

When determining that the maximum luminance value Amax is larger than the proper upper limit luminance value Xmax, the image processing section 24 shifts a luminance value of the entire images downward to thereby perform image processing such that a luminance dynamic range of the entire images is fit within the proper luminance range (step S7).

When determining in step S6 that the maximum luminance value Amax of the images is equal to or smaller than the proper upper limit luminance value Xmax, the image processing section 24 further determines whether the minimum luminance value Amin of the images is smaller than the proper lower limit luminance value Xmin (step S8).

When determining that the minimum luminance value Amin of the images is smaller than the proper lower limit luminance value Xmin, the image processing section 24 shifts the luminance value of the entire images upward to thereby perform image processing such that the luminance dynamic range of the entire images is fit within the proper luminance range (step S9).

In this way, when a luminance difference between the minimum luminance value Amin and the maximum luminance value Amax is equal to or smaller than a luminance difference between the proper lower limit luminance value Xmin and the proper upper limit luminance value Xmax, instead of the gradation conversion, the image processing section 24 performs only a luminance shift with which a minimum luminance value is equal to or larger than the proper lower limit luminance value Xmin and a maximum luminance value is equal to or smaller than the proper upper limit luminance value Xmax.

On the other hand, when determining in step S5 that (Amax−Amin)>(Xmax−Xmin), the image processing section 24 determines whether the maximum luminance value Amax of the images is larger than the proper upper limit luminance value Xmax (step S10).

When determining that the maximum luminance value Amax is equal to or smaller than the proper upper limit luminance value Xmax, the image processing section 24 further determines whether the minimum luminance value Amin of the images is smaller than the proper lower limit luminance value Xmin (step S11).

When determining in step S10 that the maximum luminance value Amax of the images is larger than the proper upper limit luminance value Xmax or when determining in step S11 that the minimum luminance value Amin of the images is smaller than the proper lower limit luminance value Xmin, the image processing section 24 generates a gradation conversion curve shown in FIG. 8 (step S12).

FIG. 8 is a diagram showing an example of a gradation conversion curve for fitting the images within the proper luminance range.

The gradation conversion curve is a conversion curve for converting the inputted minimum luminance value Amin into the proper lower limit luminance value Xmin, converting the inputted maximum luminance value Amax into the proper upper limit luminance value Xmax, and, further, converting an input luminance value between the minimum luminance value Amin and the maximum luminance value Amax into an output luminance value between the proper lower limit luminance value Xmin and the proper upper limit luminance value Xmax with a monotonous increase along the input luminance value. Consequently, the image processing section 24 is capable of performing the gradation conversion that does not invert a magnitude relation among the luminance values of the pixels forming the first image and the second images. In particular, gradation conversion such as γ conversion adjusted to a display characteristic of the monitor 3 is performed as separate processing in the image processing section 24. That is, the gradation conversion does not need to be taken into account in the processing of the luminance adjustment. Therefore, the gradation conversion is performed using the following equation 1 represented by a linear function as a monotonous increase function for calculating an output luminance value Yout from an input luminance value Yin.

$$Yout = \{(Xmax - Xmin)/(Amax - Amin)\} \times (Yin - Amin) + Xmin \quad [\text{equation 1}]$$

The gradation conversion may be performed by, for example, table reference instead of using equation 1.

Note that, in FIG. 8, assuming that pixels having luminance values smaller than the minimum luminance value Amin are absent and pixels having luminance values larger than the maximum luminance value Amax are absent in the images, only a range of the input luminance value equal to or larger than Amin and equal to or smaller than Amax is described. However, as explained below with reference to FIG. 9, when a luminance range (an excluded region) excluded from the gradation conversion is set, concerning an input of a luminance value smaller than the minimum luminance value Amin and an input of a luminance value larger than the maximum luminance value Amax, the input luminance values only have to be directly set as output luminance values.

The image processing section 24 performs the gradation conversion using the generated gradation conversion curve as explained below with reference to FIG. 12 (step S13). Consequently, a luminance distribution before the gradation conversion indicated by an alternate long and short dash line in FIG. 7 changes to a luminance distribution after the gradation conversion indicated by a solid line. That is, the luminance distribution is fit within the proper luminance range of the luminance value equal to or larger than Xmin and equal to or smaller than Xmax. FIG. 7 is a diagram showing a situation of a change in the luminance distribution by the gradation conversion.

When the processing in step S7, step S9, or step S13 is performed or when it is determined in step S8 or step S11 that the minimum luminance value Amin of the images is equal to or larger than the proper lower limit luminance value Xmin (i.e., the images are fit within the proper luminance range even if the luminance adjustment is not performed), the endoscope system performs the other image processing with the image processing section 24, generates a display signal with the output section 25, and displays the display signal on the monitor 3 (step S14).

Thereafter, the endoscope system determines whether to finish the processing (step S15). When determining not to finish the processing, the endoscope system returns to step S2 and performs the processing explained above. When determining to finish the processing, the endoscope system ends the processing.

FIG. 11 is a flowchart for explaining details of the acquisition processing for the maximum luminance value Amax and the minimum luminance value Amin in step S4 in FIG. 10. The processing is performed mainly by the brightness-range calculating section 23.

When starting the processing, first, the brightness-range calculating section 23 initializes the maximum luminance value Amax and the minimum luminance value Amin (step S21). More specifically, the brightness-range calculating section 23 substitutes 0, which is a dynamic range minimum luminance value that can be taken as a luminance value, in the maximum luminance value Amax and substitutes a dynamic range maximum luminance value Ymax (i.e., a maximum value of a luminance dynamic range and is 1023 in the case of a 10-bit signal of 0 to 1023), which can be taken as a luminance value, in the minimum luminance value Amin.

Subsequently, the brightness-range calculating section 23 reads an upper threshold Yu (satisfying Yu>Xmax) and a lower threshold Yd (satisfying Yd<Xmin) indicating a luminance range of an excluded region set in advance (or set by the user) (step S22). The excluded region is a region excluded from a target for which the maximum luminance value Amax and the minimum luminance value Amin are calculated (i.e., both of the maximum luminance value Amax and the minimum luminance value Amin are not calculated from pixels in the excluded region) and is a region excluded from a target of the gradation conversion to be performed later.

For example, in the example shown in FIG. 2, images 31 to 33 are arrayed without gaps. However, gaps in which images are not displayed sometimes occur among the images 31 to 33 (see a gap 35 in FIG. 15) depending on arrangement and structure (see FIG. 14) of the image pickup sections 11 to 13. Such gaps and the like are directly displayed without performing the gradation conversion. Therefore, the gaps are the excluded regions.

Further, a white void region and a black solid region in the images do not change to images in which details can be observed even if the gradation conversion is performed such that the regions are fit within the proper luminance range. Moreover, gradation width of the entire images is narrowed. It is difficult to observe the images. Therefore, the white void region and the black solid region are also the excluded regions.

Therefore, assuming the white void region and the black solid region and assuming that the gaps among the images 31 to 33 are displayed as white frame, black frames, and the like, processing for setting, as the excluded regions, pixels having luminance values equal to or larger than a predetermined upper threshold Yu indicating a white void and pixels having luminance values equal to or smaller than a predetermined lower threshold Yd indicating a black solid is performed as explained below.

FIG. 9 is a diagram showing an example of a luminance distribution obtained when gaps of black display are present between the forward image 31 and the right sideward image 32 and between the forward image 31 and the left sideward image 33. In the example shown in FIG. 9, a vicinity of the horizontal pixel position P1 and a vicinity of the horizontal pixel position Pr are the gaps of the black display. The luminance value is equal to or smaller than the lower threshold Yd.

Subsequently, the brightness-range calculating section 23 reads a luminance value Y of one pixel from the images (the forward image 31, the right sideward image 32, and the left sideward image 33) in appropriate order, for example, order of raster scan (step S23) and determines whether the read luminance value Y is equal to or smaller than the lower threshold Yd (step S24).

When determining that the luminance value Y is larger than the lower threshold Yd, the brightness-range calculating section 23 determines whether the luminance value Y is equal to or larger than the upper threshold Yu (step S25).

When determining that the luminance value Y is smaller than the upper threshold Yu, that is, when determining that the pixel is not in the excluded region, the brightness-range calculating section 23 determines whether the luminance value Y is smaller than the minimum luminance value Amin set at present (step S26).

When determining that the luminance value Y is smaller than the minimum luminance value Amin, the brightness-range calculating section 23 substitutes the luminance value Y in the minimum luminance value Amin (step S27).

When determining in step S26 that the luminance value Y is equal to or larger than the minimum luminance value Amin, the brightness-range calculating section 23 determines whether the luminance value Y is larger than the maximum luminance value Amax set at present (step S28).

When determining that the luminance value Y is larger than the maximum luminance value Amax, the brightness-range calculating section 23 substitutes the luminance value Y in the maximum luminance value Amax (step S29).

When determining in step S24 that the luminance value Y is equal to or smaller than the lower threshold Yd, when determining in step S25 that the luminance value Y is equal to or larger than the upper threshold Yu, when determining in step S28 that the luminance value Y is equal to or smaller than the maximum luminance value Amax, when performing the processing in step S27, or when performing the processing in step S29, the brightness-range calculating section 23 determines whether the processing for all the pixels included in the images (the forward image 31, the right sideward image 32, and the left sideward image 33) has finished (step S30).

When determining that the processing of all the pixels has not finished yet, the brightness-range calculating section 23 shifts to step S23 and performs the processing concerning next unprocessed pixel as explained above. When determining that the processing of all the pixels has finished, the brightness-range calculating section 23 returns to the processing shown in FIG. 10 from the processing.

FIG. 12 is a flowchart showing details of the gradation conversion processing in step S13 in FIG. 10. The processing is performed mainly by the image processing section 24.

When starting the processing, the image processing section 24 reads the luminance value Y of one pixel from the respective images (the forward image 31, the right sideward image 32, and the left sideward image 33) in appropriate order, for example, order of raster scan (step S41) and determines whether the read pixel is a pixel in the excluded region (step S42). As explained above, the image processing section 24 may perform the determination of the excluded region by comparing the luminance value Y of the read pixel with the lower threshold Yd and the upper threshold Yu again. Alternatively, the image processing section 24 may store a pixel position concerning the pixel determined as being in the excluded region in the processing shown in FIG. 11 and performs the determination of the excluded region by determining whether a position of the pixel read in step S41 coincides with the stored pixel position of the excluded region.

In particular, when the pixel position, which is the excluded region, is stored in the latter case, it is possible to extend and apply the determination when pixels forming boundaries between the first image and the second images are pixels having luminance values other than white pixels and black pixels, for example, gray pixels. In this case, if the pixel position, which is the excluded region, is stored in advance, it is possible to exclude the pixel position from the target of the gradation conversion in the determination in step S42.

In this way, concerning the pixels forming the boundaries between the first image and the second images, the image processing section 24 performs adjustment of the luminance values if the images are continuous (a gap, which is a non-image portion, is absent between the images). However, the image processing section 24 does not perform the adjustment of the luminance value, for example, when the gap is present between the images.

When determining that the pixel is not the pixel in the excluded region, the image processing section 24 subjects the pixel to the gradation conversion according to the gradation conversion curve shown in FIG. 8 (step S43).

When performing the processing in step S43 or when determining in step S42 that the pixel is the pixel in the excluded region, the image processing section 24 determines whether the processing has finished concerning all pixels included in the images (the forward image 31, the right sideward image 32, and the left sideward image 33) (step S44).

When determining that the processing of all the pixels has not finished yet, the image processing section 24 shifts to step S41 and performs the processing concerning the next unprocessed pixel as explained above. When determining that the processing of all the pixels has finished, the image processing section 24 returns from the processing to the processing shown in FIG. 10.

In this way, the image processing section 24 does not perform the adjustment of the luminance value concerning pixels having luminance values equal to or larger than the upper threshold Yu and pixels having luminance values equal to or smaller than the lower threshold Yd.

Figure 13:
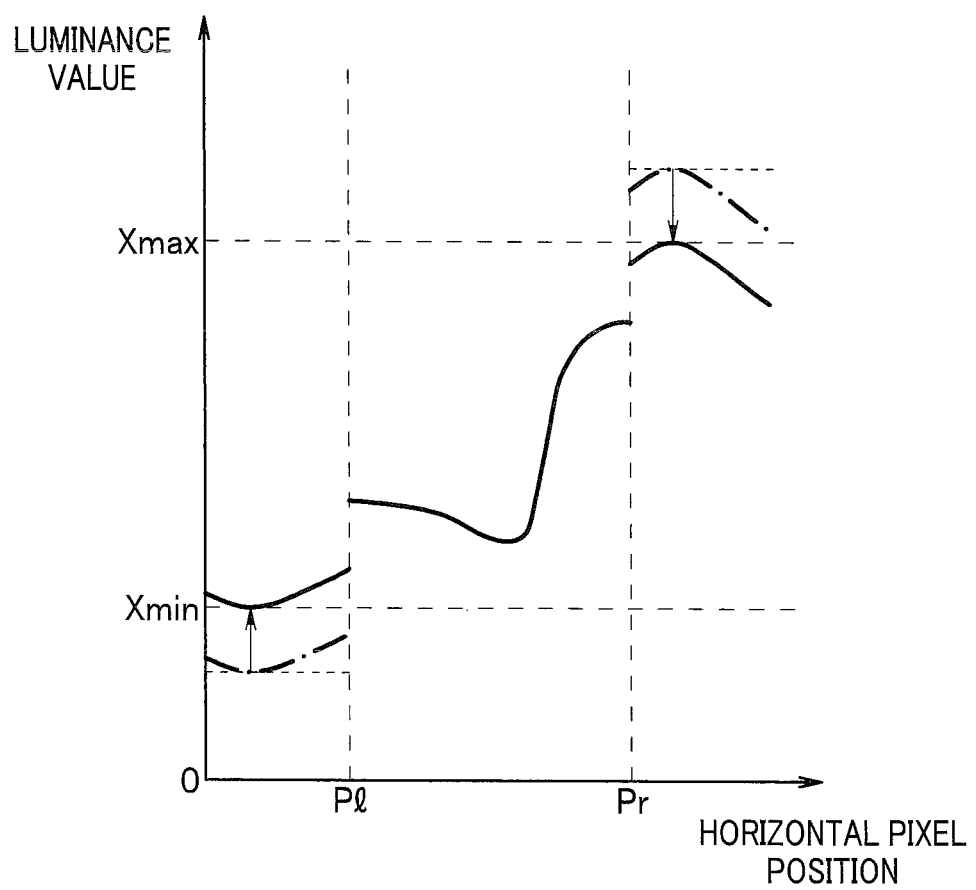
FIG. 13 is a diagram showing an example in which the luminance distribution of the images obtained in the state shown in FIG. 3 is subjected to the gradation conversion for each of the images in respective directions of fields of view in the first embodiment.

FIG. 13 is a diagram showing an example in which the luminance distribution of the images obtained in the state shown in FIG. 3 is subjected to the gradation conversion for each of the images in respective directions of fields of view.

As shown in FIG. 13, when a luminance dynamic range is equal to or larger than Xmax or equal to or smaller than Xmin in one or two images (e.g., the right sideward image 32 and the left sideward image 33) among the forward image 31, the right sideward image 32, and the left sideward image 33 and a luminance dynamic range of the remaining image (e.g., the forward image 31) is sufficiently smaller than Xmax and sufficiently larger than Xmin, the gradation conversion explained above may be individually performed on necessary images among a plurality of images. An input luminance value may be directly outputted as an output luminance value concerning an image on which the gradation conversion applied to the necessary images is not performed.

That is, necessary images among the first image (e.g., the forward image 31) and the second images (e.g., the right-sideward image 32 and the left sideward image 33) may be individually subjected to the gradation conversion such that a luminance range from a minimum luminance value to a maximum luminance value is fit within a predetermined luminance range.

By performing the gradation conversion individually on the forward image 31, the right sideward image 32, and the left sideward image 33 in this way, even if gradations of the sideward images 32 and 33 become appropriate, a situation does not occur in which a gradation of the forward image 31, which is an image in a region different from the sideward images 32 and 33, is narrowed and the forward image 31 is not appropriately represented. It is possible to simultaneously and satisfactorily observe an inner wall of a lumen close to the distal end portion of the insertion section 1a and an inner wall of a lumen far from the distal end of the insertion section 1a.

Figure 14:
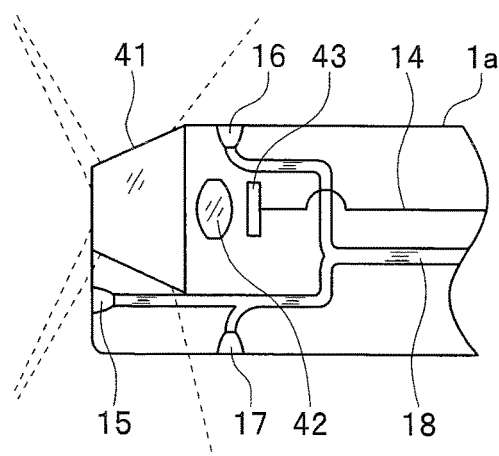
FIG. 14 is a diagram partially showing an internal configuration of an endoscope in a first modification of the first embodiment.
Figure 15:
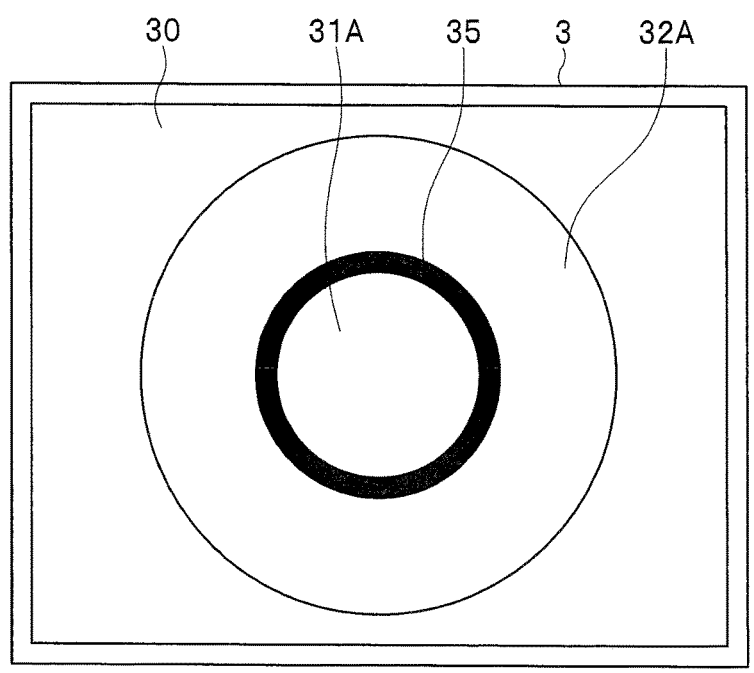
FIG. 15 is a diagram showing a display example on a monitor of an image obtained from the endoscope in the first modification of the first embodiment.

A first modification of the endoscope system is explained with reference to FIGS. 14 and 15. FIG. 14 is a diagram partially showing an internal configuration of the endoscope 1 in the first modification. FIG. 15 is a diagram showing a display example on the monitor 3 of an image obtained from the endoscope 1 in the first modification.

The distal end portion of the insertion section 1a of the endoscope 1 is provided with a compound optical system 41 that transmits and acquires a forward optical image (an image of a field of view in a region including a forward direction in a subject) and reflects and acquires an optical image (an image of a field of view in a region including a sideward direction different from the forward direction in the same subject) in a predetermined angle range (an entire circumference in a circumferential direction when the predetermined angle range is 360°) in the circumferential direction in the sideward direction and an imaging optical system 42 that forms an optical image from the compound optical system 41 on an image pickup device 43 explained below.

That is, in the modification, a first subject-image acquiring section is configured by portions that form a forward optical image of the compound optical system 41 and the imaging optical system 42 and a portion that picks up the forward optical image of the image pickup device 43. The first subject-image acquiring section is disposed to be directed forward at the distal end portion of the insertion section 1a.

A second subject-image acquiring section is configured by portions that form the sideward optical image of the compound optical system 41 and the imaging optical system 42 and a portion that picks up the sideward optical image of the image pickup device 43. The second subject-image acquiring section is disposed in a circumferential surface section of the insertion section 1a to be capable of picking up a subject image in a predetermined angle range in the circumferential direction.

In this way, both of the forward optical image and the sideward optical image in the circumferential direction are formed in different image pickup regions on the same image pickup device 43 and image pickup signals are generated.

Therefore, the first subject-image acquiring section and the second subject-image acquiring section share and include one image pickup section (the image pickup device 43). An optical image (a first subject image) of a subject present in a first field of view is formed in a part of the image pickup section and a first image pickup signal is generated. An optical image (a second subject image) of a subject present in a second field of view is formed in another part of the image pickup section and a second image pickup signal is generated.

The image pickup signals generated by the image pickup device 43 are outputted to the video processor 2 via the signal line 14. An image including a first image and second images is formed by the image forming section 20 explained above in the video processor 2 and is processed by the brightness-range calculating section 23 and the image processing section 24 (i.e., the image pickup section is electrically connected to the image forming section 20).

A distal end side of the light guide 18 branches. One branch is connected to the illuminating section 15 that radiates light in a forward direction. Another branch is connected to the illuminating section 16 that radiates light, for example, in a right sideward direction. Still another branch is connected to the illuminating section 17 that radiates light in a left sideward direction. Note that, in a configuration in the modification, a subject image in the circumferential direction is picked up concerning a sideward direction. Therefore, an illuminating section that radiates light in an upper sideward direction, an illuminating section that radiates light in a lower sideward direction, an illuminating section that radiates light in another sideward direction, or the like may be provided.

An image obtained from the endoscope 1 having such a configuration is displayed on the screen 30 of the monitor 3, for example, as shown in FIG. 15.

First, the forward optical image acquired from the compound optical system 41 is formed by the imaging optical system 42 as a circular optical image in a center of the image pickup device 43. As a result of photoelectric conversion by the image pickup device 43, a first image pickup signal of a forward field of view is generated. A circular forward image 31A is formed by the image forming section 20 on the basis of the first image pickup signal of the forward field of view.

The sideward optical image in the circumferential direction acquired by the compound optical system 41 is formed by the imaging optical system 42 as an optical image in a predetermined angle range (an annular optical image when the predetermined angle range is 360°) in a ring surrounding the circular optical image in the center explained above in the image pickup device 43. As a result of photoelectric conversion by the image pickup device 43, a second image pickup signal in a sideward field of view is generated. For example, an annular sideward image 32A in an outer circumferential section of the forward image 31A is formed by the image forming section 20 on the basis of the second image pickup signal in the sideward field of view.

Further, the gap 35 occurs between the forward image 31A and the sideward image 32A because of a configuration, disposition, and the like of the compound optical system 41. The gap 35 is a dark portion in which an optical image of a subject is not formed on the image pickup device 43. Therefore, the gap 35 assumes a black frame shape. Therefore, as explained above with reference to FIG. 9, the gap 35 is an excluded region excluded from a target on which the gradation conversion is performed.

In general, the image pickup device 43 includes a rectangular image pickup surface. However, image circles of the compound optical system 41 and the imaging optical system 42 are regions surrounded by a circle smaller than an image pickup surface as explained with reference to FIG. 15. A size and a shape of an image circle on the image pickup device 43 are known as design values if a configuration of an optical system is determined. Therefore, when the image pickup device 43 is an imager such as a CMOS capable of reading out a pixel in a desired pixel position, when readout from the image pickup device 43 is performed, an increase in speed of the readout may be achieved by reading out only pixels in the image circle. Consequently, it is possible to improve a frame rate of an image and reduce power consumption during the readout.

Further, at this point, readout from the image pickup device 43 may be not performed concerning a pixel corresponding to the gap 35 to achieve a further increase in the speed of the readout.

The image forming section 20 forms the forward image 31A as a first image in a circular shape, forms the sideward image 32A as a second image in a shape of a predetermined angle range in a ring surrounding the forward image 31A, and forms an image.

In the first modification, as in the first embodiment explained above, necessary images among the first image and the second images may be individually subjected to the gradation conversion.

For example, when the gradation conversion is individually performed in the first image and the second images, it is sufficient to perform processing for disassembling and respectively cutting out a region of the forward image (the first image) and regions of the sideward images (the second images) from the image (the image signal), performing individual kinds of gradation conversion processing same as the gradation conversion processing explained in the first embodiment respectively on the forward image (the first image) and the sideward images (the second images), and combining the processed forward image (the first image) and the sideward images (the second images) to form the original one image.

Figure 16:
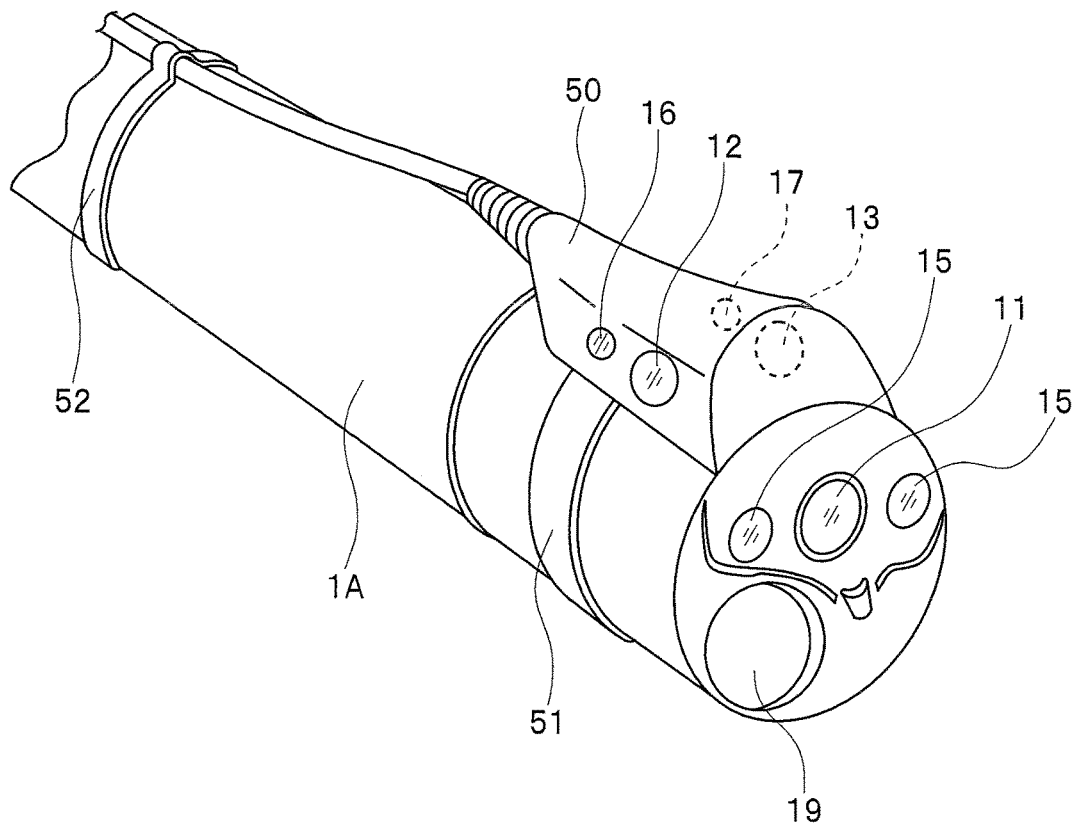
FIG. 16 is a perspective view partially showing a configuration of an endoscope in a second modification in a state in which a sideward-image acquiring unit is mounted in the first embodiment.
Figure 17:
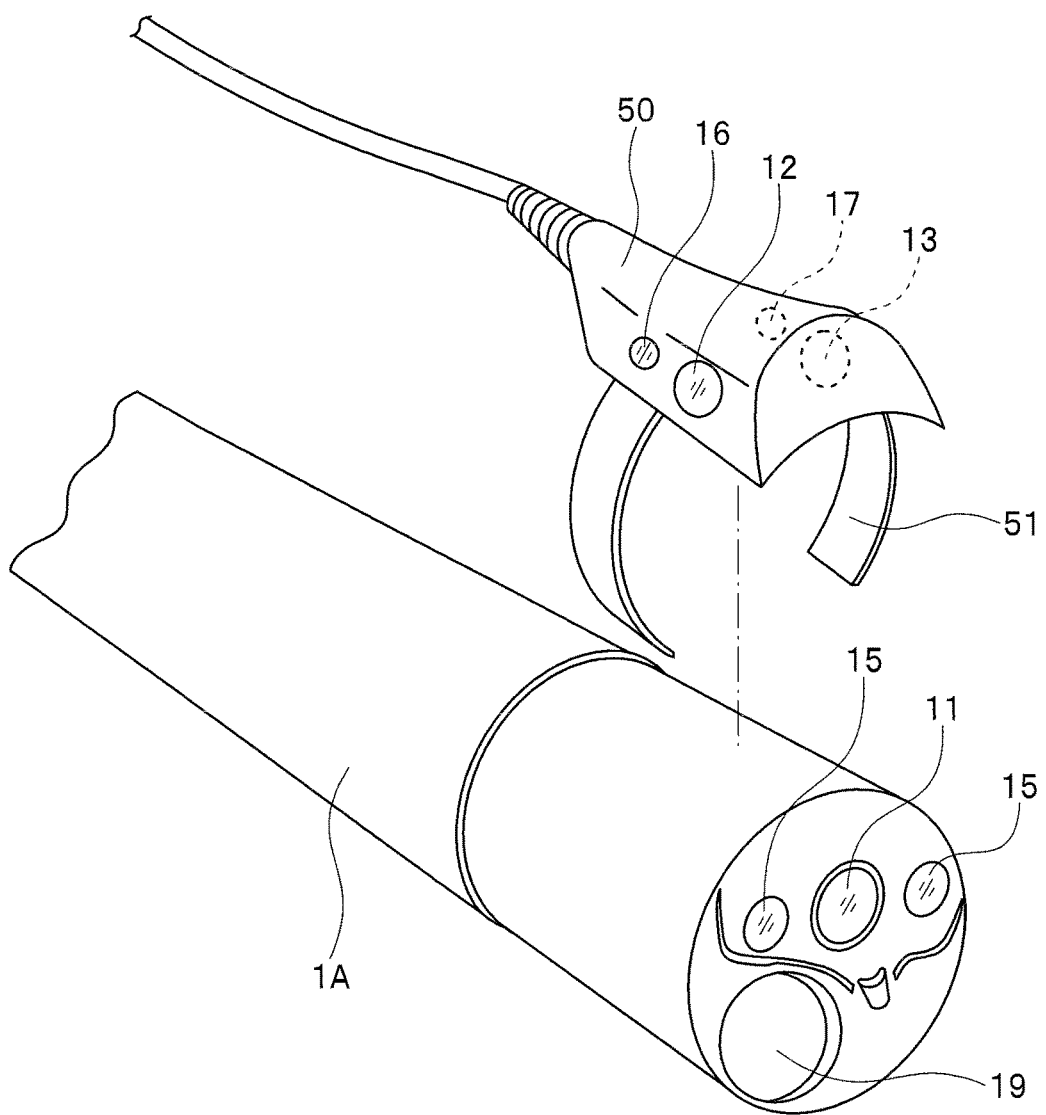
FIG. 17 is a perspective view partially showing the configuration of the endoscope in the second modification in a state in which the sideward-image acquiring unit is detached in the first embodiment.

A second modification of the endoscope system is explained with reference to FIGS. 16 and 17. FIG. 16 is a perspective view partially showing a configuration of an endoscope in the second modification in a state in which a sideward-image acquiring unit 50 is mounted. FIG. 17 is a perspective view partially showing the configuration of the endoscope in the second modification in a state in which the sideward-image acquiring unit 50 is detached.

The endoscope in the modification includes, as shown in FIGS. 16 and 17, an endoscope main body 1A and the sideward-image acquiring unit 50.

The endoscope main body 1A includes the image pickup section 11 that acquires a first image pickup signal related to the forward image 31, the illuminating section 15 that radiates light in a forward direction to an image pickup range by the image pickup section 11, and a forceps channel 19 for inserting through a treatment instrument such as forceps. The endoscope main body 1A can be used as a general front-view type endoscope as well.

The sideward-image acquiring unit 50 is detachably attached to the endoscope main body 1A.

The sideward-image acquiring unit 50 includes the image pickup section 12 that acquires a second image pickup signal related to the right sideward image 32, the illuminating section 16 that radiates light to a right sideward direction to an image pickup range by the image pickup section 12, the image pickup section 13 that acquires a second image pickup signal related to the left sideward image 33, the illuminating section 17 that radiates light in a left sideward direction to an image pickup range by the image pickup section 13, a fitting arm section 51 that fits in the endoscope main body 1A to attach the sideward-image acquiring unit 50 to the endoscope main body 1A, and a locking band 52 for locking a cord on a proximal end side of the sideward-image acquiring unit 50 to the endoscope main body 1A.

The embodiment explained above is also applicable to an endoscope configured by combining the front-view endoscope main body 1A and the side-view sideward-image acquiring unit 50 detachably attachable to the endoscope main body 1A.

Figure 18:
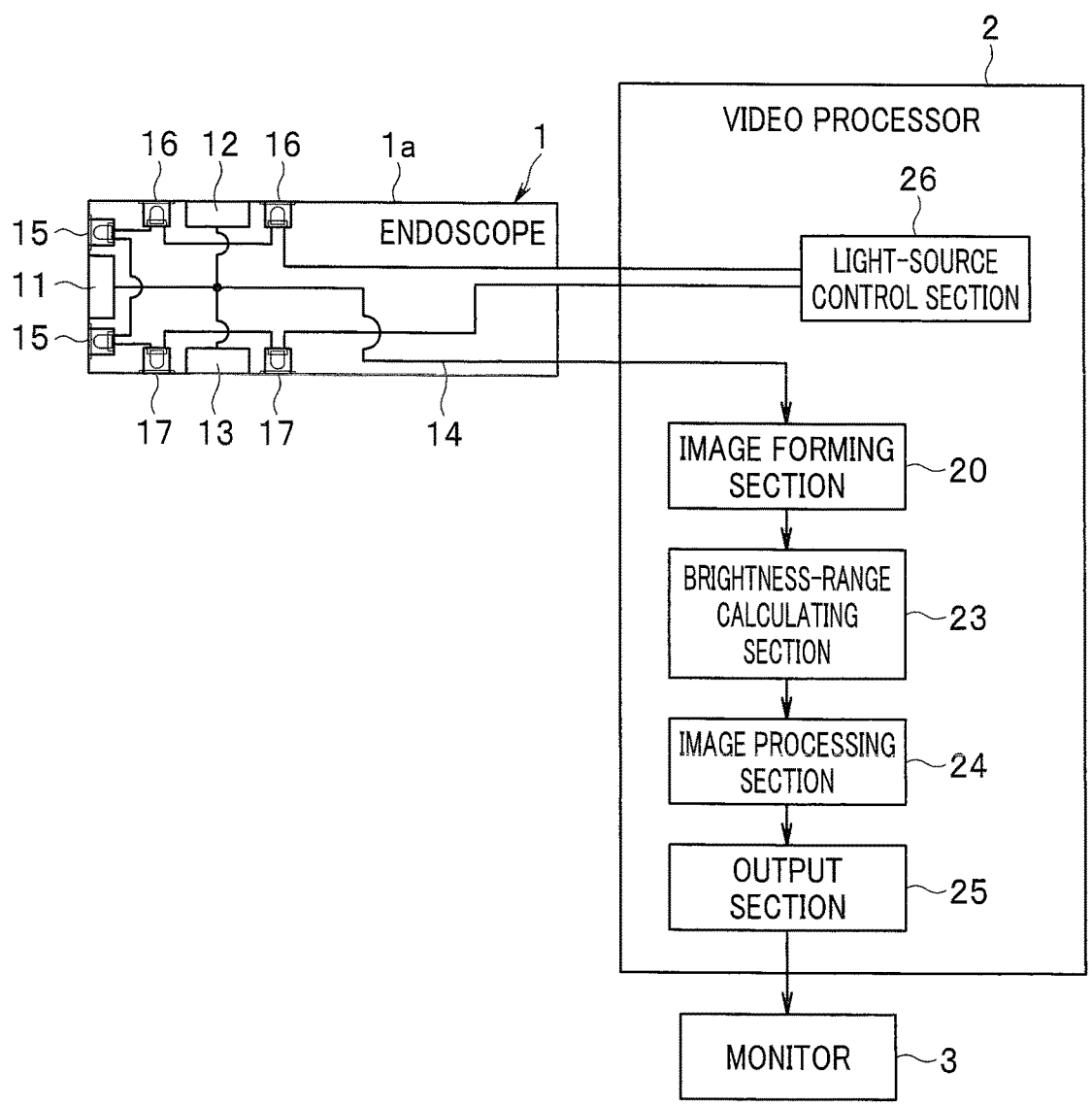
FIG. 18 is a diagram showing a modification of an endoscope system in which an illuminating section is configured by a light emitting element in the first embodiment.

Further, FIG. 18 is a diagram showing a modification of an endoscope system in which the illuminating sections 15 to 17 are configured by light emitting elements.

That is, the illuminating sections 15 to 17 shown in FIG. 18 are configured using light emitting elements such as light emitting diodes. In the video processor 2, instead of the light source section 21 and the diaphragm 22 shown in FIG. 1, a light-source control section 26 for adjusting light amounts of the illuminating sections 15 to 17 formed by the light emitting elements according to, for example, current control or pulse width modulation (PWM) is provided. By controlling the illuminating sections 15 to 17 using the light-source control section 26, light amount adjustment for simultaneously increasing or reducing light amounts of illumination lights radiated from the respective illuminating sections 15 to 17 on the subject may be performed.

According to the first embodiment explained above, the images in the plurality of fields of view are subjected to the gradation conversion such that the illumination range is fit within the predetermined luminance range (e.g., the proper luminance range). Therefore, it is possible to observe an image in a proper brightness range without spoiling shading and three-dimensional appearance of the image.

At this point, the gradation conversion for not reversing the magnitude relation among the luminance values of the pixels forming the first image and the second images is performed. Therefore, it is possible to substantially accurately maintain shading and three-dimensional appearance during image acquisition.

Further, the gradation conversion is performed according to the gradation conversion curve for converting the minimum luminance value into the proper lower limit luminance value, converting the maximum luminance value into the proper upper limit luminance value, and converting a luminance value between the minimum luminance value and the maximum luminance value into a luminance value between the proper lower limit luminance value and the proper upper limit luminance value with a monotonous increase along the input luminance value. Therefore, it is possible to fit the luminance range within the proper luminance range while maintaining the shading and the three-dimensional appearance without performing a complicated arithmetic operation.

When the input luminance value is subjected to the gradation conversion into the output luminance value using equation 1 described above, a storage capacity necessary when a table is used is unnecessary. Since equation 1 is a linear function, an advantage that a processing load of the arithmetic operation is light exists.

When the luminance dynamic range is within the proper luminance range, only the luminance shift is performed instead of the gradation conversion. Therefore, it is possible to observe an image in which a dynamic range during image acquisition is maintained.

The adjustment of the luminance values is not performed concerning the pixels having the luminance values equal to or larger than the predetermined upper threshold Yu and the pixels having the luminance values equal to or smaller than the lower threshold Yd. Therefore, it is possible to give a wide dynamic range to pixels effective for the observation of the subject.

The adjustment of the luminance values is not performed concerning the pixels forming the boundaries between the first image and the second images adjacent to each other. Therefore, the gap 35 or the like between the images is maintained at a constant luminance value. The luminance value of the gap 35 or the like does not change for each of the images. Therefore, a clear image is obtained.

Further, the images of the forward field of view and the sideward fields of view of the insertion section 1a are acquired. Therefore, it is possible to realize a super-wide angle endoscope without using an expensive and large super-wide angle lens.

The image output section generates the display signal from the image (the image signal) processed by the image processing section. Therefore, it is possible to display and observe the image on the monitor 3 or the like.

The plurality of second subject-image acquiring sections disposed in the plurality of angle positions in the circumferential direction of the insertion section 1a acquire the plurality of second image pickup signals. The image forming section 20 forms, for example, as shown in FIG. 2, the image in which the first image is present in the center and the plurality of second images are respectively arranged in the plurality of angle positions in the circumferential direction of the first image. Therefore, it is possible to observe an image coinciding with a direction of field of view during image pickup.

For example, in the configuration in which the first image pickup section and the second image pickup section are separated as shown in FIG. 1 or FIGS. 16 and 17, it is possible to acquire image pickup signals in a plurality of directions of fields of view.

For example, as shown in FIG. 14, the first image pickup signal related to the forward subject image of the insertion section 1a and the second image pickup signal related to the subject image in the predetermined angle range in the circumferential direction of the insertion section 1a are acquired. For example, as shown in FIG. 15, the image forming section 20 forms the first image in the circular shape on the basis of the first image pickup signal related to the forward subject image, forms the second images in the shape of the predetermined angle range in the ring surrounding the first image on the basis of the second image pickup signal related to the subject image in the circumferential direction, and forms the image signal (the image). In this case, as in the case explained above, it is possible to observe an image coinciding with the direction of field of view during the image pickup.

For example, as shown in FIG. 14, if the configuration in which the first subject-image acquiring section and the second subject-image acquiring section share one image pickup section is adopted, it is possible to effectively achieve a reduction in a diameter and a reduction in weight of the endoscope distal end section.

According to the configurations of the respective embodiments explained above, in the endoscope system, in particular, the endoscope system including the wide angle endoscope including the front-view observation optical system and the side-view observation optical system, it is possible to observe an image in a proper brightness range without spoiling shading and three-dimensional appearance of the image.

Note that, in the above explanation, the example in which the first subject-image acquiring section and the second subject-image acquiring section are provided in the endoscope 1 and the example in which the first subject-image acquiring section is provided in the endoscope main body 1A and the second subject-image acquiring section is provided in the sideward-image acquiring unit 50 are explained. However, the present invention is not limited to the examples. The first subject-image acquiring section and the second subject-image acquiring section include, for example, the image pickup optical systems and the image pickup devices. However, the image pickup optical systems may be disposed in the endoscope 1 (or the endoscope main body 1A and the sideward-image acquiring unit 50). The image pickup devices may be disposed in the video processor 2. In this case, optical images formed by the image pickup optical systems only have to be transmitted to the image pickup devices in the video processor 2 via a transmission optical system or the like.

The endoscope system is mainly explained above. However, the present invention may be an actuating method for actuating the endoscope system as explained above or may be a processing program for causing a computer to actuate the endoscope system as explained above, a computer-readable non-transitory recording medium that records the processing program, or the like.

Note that the present invention is not limited to the embodiment explained above per se. In an implementation stage, the constituent elements can be modified and embodied in a range not departing from the spirit of the present invention. Various focus of inventions can be formed by appropriate combinations of the plurality of constituent elements disclosed in the embodiment. For example, several constituent elements may be deleted from all the constituent elements described in the embodiment. Further, the constituent elements described in different embodiments may be combined as appropriate. In this way, it goes without saying that various modifications and applications are possible within a range not departing from the spirit of the invention.

What is claimed is:

1. An endoscope system comprising:
a video processor configured to:
   form an image of one frame including:
      a first image based on a first image pickup signal generated from an optical image of a first region of a subject picked up by an endoscope; and
      a second image based on a second image pickup signal generated from an optical image of a second region of the subject picked up by the endoscope;
   detect a minimum luminance value and a maximum luminance value in the first image included in the image of the one frame;
   detect a minimum luminance value and a maximum luminance value in the second image included in the image of the one frame; and
   with respect to each of the first image and the second image,
      determine whether or not a luminance range of the each of the first image and the second image is larger than a predetermined luminance range,
         wherein the luminance range of the each of the first image and the second image is defined by a difference value between the maximum luminance value of the each of the first image and the second image and the minimum luminance value of the each of the first image and the second image,
         wherein the predetermined luminance range is defined by a difference value between a predetermined luminance upper limit value and a predetermined luminance lower limit value, and
         wherein the predetermined luminance upper limit value is smaller than a dynamic range maximum luminance value, the predetermined luminance lower limit value is larger than a dynamic range minimum luminance value, and the predetermined luminance upper limit value is larger than the predetermined luminance lower limit value;
      perform luminance shift processing of shifting luminance of the each of the first image and the second image so as to have the minimum luminance value of the each of the first image and the second image coincide with the predetermined luminance lower limit value, in response to determining that the luminance range of the each of the first image and the second image is equal to or smaller than the predetermined luminance range, and determining that the minimum luminance value of the each of the first image and the second image is smaller than the predetermined luminance lower limit value; and
      perform luminance shift processing of shifting luminance of the each of the first image and the second image so as to have the maximum luminance value of the each of the first image and the second image coincide with the predetermined luminance upper limit value, in response to determining that the luminance range of the each of the first image and the second image is equal to or smaller than the predetermined luminance range, and determining that the maximum luminance range of the each of the first image and the second image is larger than the predetermined luminance upper limit value.

2. The endoscope system according to claim 1,
wherein the video processor is configured to:
execute gradation conversion processing conforming to a predetermined gradation conversion curve; and
perform the gradation conversion processing on an image not fit within the predetermined luminance range among the first image and the second image included in the image of the one frame.

3. The endoscope system according to claim 2,
wherein the video processor is configured to perform the gradation conversion according to, as the predetermined gradation conversion curve, a gradation conversion curve for converting the minimum luminance value into a proper lower limit luminance value, converting the maximum luminance value into a proper upper limit luminance value, and converting a luminance value between the minimum luminance value and the maximum luminance value into a luminance value between the proper lower limit luminance value and the proper upper limit luminance value with a monotonous increase along an input luminance value.

4. The endoscope system according to claim 3,
wherein, when the minimum luminance value of pixels forming the first image and the second image is represented as Amin, the maximum luminance value of the pixels is represented as Amax, the proper lower limit luminance value of the pixels is represented as Xmin, and the proper upper limit luminance value of the pixels is represented as Xmax, the video processor is configured to apply a following equation to an input luminance value Yin to thereby subject the input luminance value Yin to the gradation conversion into an output luminance value Yout:

$$Yout = \{(Xmax - Xmin)/(Amax - Amin)\} \times (Yin - Amin) + Xmin$$

5. The endoscope system according to claim 2,
wherein the video processor is configured to exclude, from targets of the luminance shift processing and the gradation conversion processing, a pixel forming a boundary between the first image and the second image.

6. The endoscope system according to claim 1,
wherein the video processor is configured to not perform adjustment of the luminance value concerning a pixel having a luminance value equal to or larger than a predetermined upper threshold and a pixel having a luminance value equal to or smaller than a predetermined lower threshold.

7. The endoscope system according to claim 1,
wherein the first image is acquired by a first image sensor in an insertion section of the endoscope inserted into an inside of the subject, the first image sensor picking up the optical image of the first region of the subject including a forward direction along a longitudinal direction of the insertion section, and
wherein the second image is acquired by a second image sensor picking up the optical image of the second region of the subject including a sideward direction crossing the longitudinal direction of the insertion section.

8. The endoscope system according to claim 7,
wherein the second image sensor is disposed in plurality in a plurality of angle positions in a circumferential direction of the insertion section, and
wherein the video processor is configured to arrange the second image in plurality respectively in the plurality of angle positions in the circumferential direction of the first image centering on the first image to form the image of the one frame.

9. The endoscope system according to claim 1,
wherein the video processor is configured to generate a display signal for causing a display to display the image for one frame that has been processed.

10. The endoscope system according to claim 1, further comprising:
the endoscope, wherein the endoscope comprises:
an insertion section configured to be inserted into an inside of the subject;
a first image sensor disposed to be directed forward at a distal end portion of the insertion section and configured to pick up the optical image of the first region of the subject; and
a second image sensor disposed in a circumferential surface section of the insertion section to be capable of acquiring an image in a predetermined angle range in a circumferential direction and configured to pick up the optical image of the second region of the subject which is different from the first region, and
wherein the video processor is configured to form the image of one frame such that the first image in a circular shape and the second image in plurality in a shape of a predetermined angle range in a ring surrounding the first image.

11. The endoscope system according to claim 10,
wherein the first image sensor is configured to photoelectrically convert the optical image of the first region to generate the first image pickup signal,
wherein the second image sensor is configured to photoelectrically convert the optical image of the second region to generate the second image pickup signal,
wherein the first image sensor and the second image sensor are electrically connected to the video processor.

12. The endoscope system according to claim 10,
wherein the first image sensor and the second image sensor share and include one image pickup surface, the optical image of the first region being formed in a part of the image pickup surface to generate the first image pickup signal, and the optical image of the second region being formed in another part of the image pickup surface to generate the second image pickup signal.

13. The endoscope system according to claim 1, further comprising:
a light source configured to emit illumination light having brightness based on a brightness evaluation result of the image of the one frame to the first region and the second region.

14. An actuating method for an endoscope system, the actuating method comprising:
forming an image of one frame including:
a first image based on a first image pickup signal generated from an optical image of a first region of a subject picked up by an endoscope; and
a second image based on a second image pickup signal generated from an optical image of a second region of the subject picked up by the endoscope;
detecting a minimum luminance value and a maximum luminance value in the first image included in the image of the one frame;
detecting a minimum luminance value and a maximum luminance value in the second image included in the image of the one frame; and with respect to each of the first image and the second image,
 determining whether or not a luminance range of the each of the first image and the second image is larger than a predetermined luminance range,
  wherein the luminance range of the each of the first image and the second image is defined by a difference value between the maximum luminance value of the each of the first image and the second image and the minimum luminance value of the each of the first image and the second image,
  wherein the predetermined luminance range is defined by a difference value between a predetermined luminance upper limit value and a predetermined luminance lower limit value, and
  wherein the predetermined luminance upper limit value is smaller than a dynamic range maximum luminance value, the predetermined luminance lower limit value is larger than a dynamic range minimum luminance value, and the predetermined luminance upper limit value is larger than the predetermined luminance lower limit value;
 perform luminance shift processing of shifting luminance of the each of the first image and the second image so as to have the minimum luminance value of the each of the first image and the second image coincide with the predetermined luminance lower limit value, in response to determining that the luminance range of the each of the first image and the second image is equal to or smaller than the predetermined luminance range, and determining that the minimum luminance value of the each of the first image and the second image is smaller than the predetermined luminance lower limit value; and
 perform luminance shift processing of shifting luminance of the each of the first image and the second image so as to have the maximum luminance value of the each of the first image and the second image coincide with the predetermined luminance upper limit value, in response to determining that the luminance range of the each of the first image and the second image is equal to or smaller than the predetermined luminance range, and determining that the maximum luminance range of the each of the first image and the second image is larger than the predetermined luminance upper limit value.

15. A non-transitory computer-readable medium storing instructions that cause a computer to at least perform:
 forming an image of one frame including:
  a first image based on a first image pickup signal generated from an optical image of a first region of a subject picked up by an endoscope; and
  a second image based on a second image pickup signal generated from an optical image of a second region of the subject picked up by the endoscope;
 detecting a minimum luminance value and a maximum luminance value in the first image included in the image of the one frame;
 detecting a minimum luminance value and a maximum luminance value in the second image included in the image of the one frame; and
 with respect to each of the first image and the second image,
  determining whether or not a luminance range of the each of the first image and the second image is larger than a predetermined luminance range,
   wherein the luminance range of the each of the first image and the second image is defined by a difference value between the maximum luminance value of the each of the first image and the second image and the minimum luminance value of the each of the first image and the second image,
   wherein the predetermined luminance range is defined by a difference value between a predetermined luminance upper limit value and a predetermined luminance lower limit value, and
   wherein the predetermined luminance upper limit value is smaller than a dynamic range maximum luminance value, the predetermined luminance lower limit value is larger than a dynamic range minimum luminance value, and the predetermined luminance upper limit value is larger than the predetermined luminance lower limit value;
  perform luminance shift processing of shifting luminance of the each of the first image and the second image so as to have the minimum luminance value of the each of the first image and the second image coincide with the predetermined luminance lower limit value, in response to determining that the luminance range of the each of the first image and the second image is equal to or smaller than the predetermined luminance range, and determining that the minimum luminance value of the each of the first image and the second image is smaller than the predetermined luminance lower limit value; and
  perform luminance shift processing of shifting luminance of the each of the first image and the second image so as to have the maximum luminance value of the each of the first image and the second image coincide with the predetermined luminance upper limit value, in response to determining that the luminance range of the each of the first image and the second image is equal to or smaller than the predetermined luminance range, and determining that the maximum luminance range of the each of the first image and the second image is larger than the predetermined luminance upper limit value.

* * * * *